US007935790B2

(12) United States Patent
Moritz et al.

(10) Patent No.: US 7,935,790 B2
(45) Date of Patent: May 3, 2011

(54) REAGENTS FOR THE DETECTION OF PROTEIN PHOSPHORYLATION IN T-CELL RECEPTOR SIGNALING PATHWAYS

(75) Inventors: Albrecht Moritz, Salem, MA (US); Roberto Polakiewicz, Lexington, MA (US); John Edward Rush, Beverly, MA (US); Kimberly Lee, Seattle, WA (US)

(73) Assignee: Cell Singaling Technology, Inc., Danvers, MA (US)

( * ) Notice: Subject to any disclaimer, the term of this patent is extended or adjusted under 35 U.S.C. 154(b) by 923 days.

(21) Appl. No.: 11/503,336

(22) Filed: Aug. 11, 2006

(65) Prior Publication Data
US 2007/0059845 A1    Mar. 15, 2007

Related U.S. Application Data

(63) Continuation of application No. PCT/US04/32511, filed on Oct. 4, 2004.

(51) Int. Cl.
*C07K 16/00* (2006.01)
*C07K 16/18* (2006.01)
(52) U.S. Cl. .................. 530/387.1; 530/387.9
(58) Field of Classification Search .................. None
See application file for complete search history.

(56) References Cited

U.S. PATENT DOCUMENTS

| | | |
|---|---|---|
| 3,940,475 A | 2/1976 | Gross |
| 4,289,747 A | 9/1981 | Chu et al. |
| 4,349,893 A | 9/1982 | Wiegman et al. |
| 4,376,110 A | 3/1983 | David et al. |
| 4,474,893 A | 10/1984 | Reading et al. |
| 4,634,664 A | 1/1987 | Oestberg |
| 4,634,666 A | 1/1987 | Engleman et al. |
| 4,659,678 A | 4/1987 | Forrest et al. |
| 4,676,980 A | 6/1987 | Segal et al. |
| 4,727,022 A | 2/1988 | Skold et al. |
| 4,816,397 A | 3/1989 | Boss et al. |
| 4,816,567 A | 3/1989 | Cabilly et al. |
| 4,946,778 A | 8/1990 | Ladner et al. |
| 5,004,692 A | 4/1991 | Tso et al. |
| 5,092,885 A | 3/1992 | Yamada et al. |
| 5,112,946 A | 5/1992 | Maione et al. |
| 5,192,744 A | 3/1993 | Bouck et al. |
| 5,202,352 A | 4/1993 | Okada et al. |
| 5,225,539 A | 7/1993 | Winter |
| 5,260,203 A | 11/1993 | Ladner et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,585,089 A | 12/1996 | Queen et al. |
| 5,675,063 A | 10/1997 | Knight et al. |
| 5,677,427 A | 10/1997 | Goldenberg et al. |
| 5,693,761 A | 12/1997 | Queen et al. |
| 5,693,762 A | 12/1997 | Queen et al. |
| 5,789,208 A | 8/1998 | Sharon |
| 5,969,108 A | 10/1999 | McCafferty et al. |
| 6,103,889 A | 8/2000 | Whitlow et al. |
| 6,120,767 A | 9/2000 | Reagan et al. |
| 6,150,584 A | 11/2000 | Kucherlapati et al. |
| 6,180,370 B1 | 1/2001 | Queen et al. |
| 6,329,508 B1 | 12/2001 | Friden et al. |
| 6,331,415 B1 | 12/2001 | Cabilly et al. |
| 6,335,163 B1 | 1/2002 | Sharon et al. |
| 6,355,245 B1 | 3/2002 | Evans et al. |
| 6,395,718 B1 | 5/2002 | Slusher et al. |
| 6,407,213 B1 | 6/2002 | Carter et al. |
| 6,441,140 B1 | 8/2002 | Comb et al. |
| 6,462,075 B1 | 10/2002 | Bowen et al. |
| 6,465,431 B1 | 10/2002 | Thorn et al. |
| 6,475,784 B1 | 11/2002 | Papkoff et al. |
| 6,482,802 B1 | 11/2002 | Hu et al. |
| 6,482,810 B1 | 11/2002 | Brem et al. |
| 6,500,431 B1 | 12/2002 | Gill et al. |
| 6,500,924 B1 | 12/2002 | Brooks et al. |
| 6,518,298 B2 | 2/2003 | Green et al. |
| 6,521,439 B2 | 2/2003 | Folkman et al. |
| 6,525,019 B2 | 2/2003 | D'Amato et al. |
| 6,538,103 B1 | 3/2003 | Ji et al. |
| 6,544,758 B2 | 4/2003 | O'Reilly et al. |

(Continued)

FOREIGN PATENT DOCUMENTS
EP    0120694    3/1984
(Continued)

OTHER PUBLICATIONS

PharMingen (Transduction Laboratories and PharMingen 1999 Cell Biology Sourcebook, 1999, pp. 242-245).*
Glenney et al (J of Immunological Methods, 1988, 109:277-285).*
U.S. Appl. No. 10/408,486, filed Jul. 4, 2003, Crosby et al.
U.S. Appl. No. 10/781,047, filed Feb. 17, 2004, Gygi et al.
U.S. Appl. No. 10/634,581, filed May 8, 2003, Johnson et al.
U.S. Appl. No. 10/821,234, filed Jul. 4, 2004, Labat et al.
U.S. Appl. No. 11/077,717, filed Oct. 3, 2005, Lam et al.
U.S. Appl. No. 11/089,368, filed Mar. 25, 2005, Ledbetter et al.

(Continued)

*Primary Examiner* — Laura B Goddard
(74) *Attorney, Agent, or Firm* — Nancy Chiu Wilker

(57) ABSTRACT

The invention discloses 95 novel phosphorylation sites identified in signal transduction proteins and pathways downstream of the T-cell receptor, and provides phosphorylation-site specific antibodies and heavy-isotope labeled peptides (AQUA peptides) for the selective detection and quantification of these phosphorylated sites/proteins, as well as methods of using the reagents for such purpose. Among the phosphorylation sites identified are sites occurring in the following protein types: Actin Binding proteins, Adaptor/Scaffold proteins, Adhesion proteins, Calcium-binding proteins, Cell Cycle Regulation or Channel proteins, Chaperones, Cofactor proteins, Cytoskeletal proteins, DNA Binding proteins, G protein or GTPase Activating proteins, Ligases, Lipid Kinases and Binding proteins, Oxidoreductases, Protein Kinases, Protein Phosphatases, Receptor proteins, RNA Binding proteins, Transcription Factor/Initiation Complex proteins, Transcription Coactivator/Corepressor proteins, Translation Initiation Complex proteins, Ubitquitin Conjugating System proteins, and Vesicle proteins.

6 Claims, 9 Drawing Sheets

U.S. PATENT DOCUMENTS

| | | |
|---|---|---|
| 6,544,947 B2 | 4/2003 | Holaday et al. |
| 6,548,477 B1 | 4/2003 | Olson et al. |
| 6,548,640 B1 | 4/2003 | Winter et al. |
| 6,559,126 B2 | 5/2003 | Tournaire et al. |
| 6,569,845 B1 | 5/2003 | Futamura et al. |
| 6,573,256 B2 | 6/2003 | Bishop et al. |
| 6,783,961 B1 | 8/2004 | Edwards et al. |
| 6,867,007 B2 | 3/2005 | Kauvar et al. |
| 6,884,869 B2 | 4/2005 | Senter et al. |
| 6,979,557 B2 | 12/2005 | Isogai et al. |
| 7,060,268 B2 | 6/2006 | Andya et al. |
| 7,109,000 B2 | 9/2006 | Edinger et al. |
| 7,198,896 B2 | 4/2007 | Rush et al. |
| 7,300,753 B2 | 11/2007 | Rush et al. |

FOREIGN PATENT DOCUMENTS

| | | |
|---|---|---|
| EP | 1184665 | 9/1986 |
| EP | 0239400 | 9/1987 |
| EP | 0404097 | 12/1990 |
| EP | 1718977 | 10/2008 |
| WO | WO 84/03508 | 9/1984 |
| WO | WO 85/03508 | 8/1985 |
| WO | WO 86/01533 | 3/1986 |
| WO | WO 91/10741 | 7/1991 |
| WO | WO 91/17271 | 11/1991 |
| WO | WO 92/01047 | 1/1992 |
| WO | WO 93/11161 | 6/1993 |
| WO | WO 93/12227 | 6/1993 |
| WO | WO 95/20401 | 8/1995 |
| WO | WO 96/27011 | 6/1996 |
| WO | WO 02/00729 | 3/2002 |
| WO | WO 03/016861 | 2/2003 |
| WO | WO 03/089474 | 10/2003 |
| WO | WO 03/106644 | 12/2003 |
| WO | WO 2004/009618 | 1/2004 |
| WO | WO 2004/039963 | 5/2004 |
| WO | WO 2004/066957 | 8/2004 |
| WO | WO 2004/091658 | 10/2004 |
| WO | WO 2005/056825 | 6/2005 |
| WO | WO 2005/083444 | 9/2005 |

OTHER PUBLICATIONS

U.S. Appl. No. 11/049,630, filed Feb. 2, 2005, McKinsey et al.
Abu-Duhier et al., "Identification of novel FLT-3 Asp835 mutations in adult acute myeloid leukemia," Br. J. Haematol. 113: 983-988 (2001).
Hardy, et al., "Clinical and Molecular Genetic Analysis of 19 Wolfram Syndrome Kindreds Demonstrating a Wide Spectrum of Mutations in WFS1," Am. J. Hum. Genet. 65:1279-1290 (1999).
Dessein, et al., "Severe Hepatic Fibrosis in Schistoma mansoni Infection Is Controlled by a Major Locus That Is Closely Linked to the Interferon-γ Receptor Gene," Am. J. Hum. Genet. 65: 709-721 (1991).
Di Barletta, et al., "Different Mutations in the LMNA Gene Cause Autosomal Dominant and Autosomal Recessive Emery-Dreifuss Muscular Dystrophy," Am. J. Hum. Genet. 66:1407-1412 (2000).
Ebrahimi, et al., "Murine Gammaherpesvirus-68 Infection Causes Multi-Organ Fibrosis and Alters Leukocyte Trafficking in Interferon-γ Receptor Knockout Mice," American Journal of Pathology, 158(6): 2117-2125 (Jun. 2001).
Jemal, et al., "Cancer Statistics 2005," CA: A Cancer Journal for Clinicians, 55(1): 10-30 (Jan./Feb. 2005).
Pollard, et al., "Using Single-Gene Deletions to Identify Checkpoints in the Progression of Systemic Autoimmunity," Annals of the New York Academy of Sciences 987: 236-239 (Apr. 2003).
Jaskiewicz, et al., "Expression of p53 Tumor Suppressor Gene, Oncoprotein c-erbB-2, Cellular Proliferation and Differentiation n Malignant and Benign Pancreatic Lesions," Anticancer Research 14: 1919-1922 (1994).
Agarwal, et al., "Inositol Hexaphosphate Inhibits Constitutive Activation of Nf-xB in Androgen-independent Human Prostate Carcinoma DU145 Cells," Anticancer Research 23: 3855-3862 (2003).
Arias-Romero, et al., "A tale of two Paks," Biol. Cell 100: 97-108 (2008).

Bache, et al., "Phosphorylation of Hrs downstream of the epidermal growth factor receptor," Eur. J. Biochem 269: 3881-3881 (2002).
Belsches, et al., "Role of c-Src Tyrosine Kinase in EEGF-Induced Mitogenesis," Frontiers in Bioscience 269: 3881-3887 (Oct. 15, 1997).
G-Amlak, et al., "Reguation of myeloma cell growth through Akt/ Gsk3/forkhead signaling pathway," Biochemical and Biophysical Research Sommunications 297: 760-764 (2002).
Radaeva, et al., "Interferon-γ inhibits interferon-α signalling in hepatic cells: evidence for the involvement of STAT1 induction and hyperexpression of STAT1 in chronic hepatitis C," Biochem J. 379: 199-208 (2004).
Awasthi, et al., "Novel Function of Human RLIP76: ATP-Dependent Transport of Glutathione Conjugates and Doxorubicin", Biochemistry 39: 9327-9334 (2000).
Jagani, et al., "FoxO tumor suppressors and BCR-ABL-induced leukemia: A matter of evasion of apoptosis," Biochimica et Biophysica Acta 1785: 63-84 (2008).
Hashimoto, et al., "The Breakpoint Cluster Region Gene on Chromosome 22q11 Is Associated with Bipolar Disorder," Biol Psychiatry 57(10): 1097-1102 (May 15, 2005).
Bird, et al., "Single-Chain Antigen-Binding Proteins," Science 242: 423-426 (Oct. 21, 1988).
Blood, et al., "Tumor interactions with the vasculature: angiogenesis and tumor metastasis," Biochemica et Biophysica Acta 1032: 89-118 (1990).
Awasthi, et al., "RLIP76, a non-ABC transporter, and drug resistance in epilepsy," BMC Neuroscience 6(61): 1-11 (2005).
Boder, et al., "Yeast surface display for screening combinatorial polypeptide libraries", Nature Biotechnology 15: 553-557 (Jun. 1997).
Bordin, et al., "Band 3 is an anchor protein and a target for SHP-2 tyrosine phosphatase in human erythrocytes," Blood 100(1): 276-282 (Jul. 1, 2002).
Brand, et al., "Fluorescence Probes for Structure1," Annu.Rev. Biochem. 41:843-868 (1972).
Brennan, et al., "Preparation of Bispecific Antibodies by Chemical Recombination of Monoclonal Immunoglobulin G1 Fragments," Science 229: 81-83 (Jul. 5, 1985).
Byers et al., "Rationale for clinical use of immunotoxins in cancer and autoimmune disease," Seminars in Cell Biology 2:59-70 (1991).
Calalb, et al.,"Tyrosine Phosphorylation of Focal Adhesion Kinase at Sites in the Catalytic Domain Regulates Kinase Activity: a Role for Src Family Kinases," Molecular and Cellular Biology 15(2): 954-963 (Feb. 1995).
Grand, et al., "p53-Binding Protein 1 Is Fused to the Platelet-Derived Growth Factor Receptor B in a Patient with a t(5;15)(q33;q22) and a Imagine-Responsive Eosinophilic Myeloproliferative Disorder," Cancer Research 64: 7216-7219 (Oct. 15, 2004).
Carr, et al., "The Need for Guidelines in Publication of Peptide and Protein Identification Data," Molecular & Cellular Proteomics 3(6): 531-533 (2004).
Cell Signaling Technology, "Phospho-PLCgamma1 (Tyr783) Antibody," 2007 Cell Signaling Technology, Inc., Jul. 2000, 1-3.
Accili et al., "FoxOs at the Crossroads of Cellular Metabolism, Differentiation, and Transformation," Cell 117: 421-426 (May 14, 2004).
Chow et al., "Measurement of MAP Kinase Activation by Flow Cytometry Using Phospho-Specific Antibodies to MEK and ERK: Potential for Pharmacodynamic Monitoring of Signal Transduction Inhibitors", Cytometry (Communications in Clinical Cytometry) 46: 72-78 (2001).
Coia, et al., "Panning and selection of proteins using ribosome display", Journal of Immunological Methods 254: 191-197 (2001).
Crook, et al.,"Repressed by a NuRD", Nature Cel Biology 8(3): 212-214 (Mar. 2006).
Cross, et al.,"Serine/Threonine Protein Kinases and Apoptosis", Experimental Cell Research 256: 34-41 (2000).
Czernik, et al.,"Production of Phosphorylation State-Specific Antibodies", Methods in Enzymology 201: 264-283 (1991).
Daley, et al, "Induction of Chronic Myelogenous Leukemia in Mice by the P210bcr/abl Gene of the Philadelphia Chromosome," Science 247: 824-830 (1990).

Denslow, et al., "The human Mi-2/NuRD complex and gene regulation", Oncogene 26: 5433-5438 (2007).
Dorahy, et al., "Capture by chemical crosslinkers provides evidence that integrin allbfl3 forms complex with protein tyrosine kinases in intact platelets" Biochem J. 389: 481-490 (1995).
Druker, et al., "Imatinib as a Paradigm of Targeted Therapies," Adv. Cancer Res. 91: 1-30 (2004).
Edgar, et al., "Flotillin-1: gene structure c DNA cloning from human lung and the identification of alternative polyadenylation signals," The international Journal of Biochemisty & Cell Biology 33: 53-64 (2001).
Blanton, et al., "Schistosomal hepatic fibrosis and the interferon gamma receptor: a linkage analysis using single-nucleotide polymorphic markers", European Journal of Human Genetics 13: 660-668 (2005).
Song, et at., "Lamin A/C mutations associated with familial and sporadic cases of dilated cardiomyopathy in Koreans", Experimental and Molecular Medicine 39( 1): 114-120 (Feb. 2007).
Fanger, et al., "Bispecific antibodies and targeted cellular cytotoxicity", Immunol Today 12(2): 51-4 (Feb. 1991).
Vadlamudi, et al., "Heregulin and HER2 signaling selectively activates c-Src phosphorylation at tyrosine 215" FEBS Letters 543:76-80 (2003).
Yang, et al "ERK promotes tumorigenesis by inhibiting FOXO3a via MDM2-mediated degradation." Nat Cell Biol. 10(2):138-48 (Feb. 2008).
Fujita N. et al., "MTA3 and the Mi-2/NuRD complex regulate cell fate during B lymphocyte differentiation." Cell 119: 75-86 (2004).
Fujita N. et al., "MTA3; a Mi-2/NuRD Complex Subunit, Regulates an Invasive Growth Pathway in Breast Cancer." Cell 113: 207-19 (Apr. 18, 2003).
Meinhart, et al "A Structural Perspective of CTD Function." Genes and Development 19: 1401-1415 (2005).
Gerber et al., "Absolute quantification of proteins and phosphoproteins from cell lysates by tandem MS," PNAS 100(12): 6940-6945 (Jun. 10, 2003).
Graves et al. "Protein phosphorylation and signal transduction," Pharmacol. Ther. 82(2-3): 111-121 (1999).
Griffiths et al. "Human anti-self antibodies with high specificity from phage display libraries." EMBO Journal. 129(2): 725-734 (1993).
Griffiths et al. "Isolation of high affinity human antibodies directly from large synthetic repertoires," EMBO J. 13(14): 3245-3260 (1994).
Gruber et al. "Efficient tumor cell lysis mediated by a bispecific single chain antibody expressed in *Escherichia coli*." J. Immunol., 152: 5368-5374 (1994).
Gu et al. "Phosphotyrosine profiling identifies the KG-1 cell line as a model for the study of FGFR1 fusions in acute myeloid leukemia." Blood, 108(13): 4202-4204, supplemental table 1 (Dec. 15, 2006).
Hanes J. et al. "Picomolar affinity antibodies from a fully synthetic naive library selected and evolved by ribosome display." Nat. Biotechnol. 18:1287-92 (Dec. 2000).
Heessen S., Fornerod M., "The inner nuclear envelope as a transcription factor resting place," EMBO Rep. 8(10): 914-918 (2007).
Kakumu, et al "Interferon-gamma receptors on T cells in patients with chronic liver disease." Hepatogastroenterology 35: 158-61 (Aug. 1988).
Hollinger et al., "Diabodies: small bivalent and bispecific antibody fragments." Proc. Natl. Acaf. Sci. USA, 90: 6444-6448 (1993).
Burwinkel et al "Phosphorylase-kinase-deficient liver glycogenosis with an unusual biochemical phenotype in blood cells associated with a missense mutation in the beta subunit gene (PHKB)." Hum Genet. 101: 170-174 (Dec. 1997).
Blume-Jensen et al., "Oncogenic kinase signalling." Nature 411: 355-65 (May 2001).
Huse w. "Generation of a Large Combinatorial Library of the Immunoglobulin Repertoire in Phage Lambda." Science 246: 1275-1281 (1989).
Ingber et al., "Inhibition of Angiogenesis Through Modulation of Collagen Metabolism," Lab. Invest. 59: 44-51 (1988).

Htun Van Der Horst, et al "Tyrosine phosphorylation of PYK2 mediates heregulin-induced glioma invasion: novel heregulin/HER3-stimulated signaling pathway in glioma." Int. J Cancer 113(5): 689-98 (Feb. 20, 2005).
Irby et al., "Role of Src expression and activation in human cancer." Oncogene 16: 5636-642 (2000).
Jullien-Flores "Bridging Ral GTPase to Rho pathways RLIP76, a Ral effector with CDC42/Rac GTPase-activating protein activity." J Cell Chem 270(38): 22473-22477 (Sep. 22, 1995).
Hu, et al "HSF-1 interacts with Ral-binding protein 1 in a stress-responsive, multiprotein complex with HSP90 in vivo" J Cell Chem. 278(19): 17299-17306 (May 9, 2003).
Birkenkamp, et al "FOXO3a induces differentiation of Bcr-Abl-transformed cells through transcriptional down-regulation of Id1." J Biol. Chem. 282(4): 2211-2220 (Jan. 26, 2007).
Goldfinger, et al "RLIP76 (RalBP1) is an R-Ras effector that mediates adhesion-dependent Rac activation and cell migration." J Cell Biol. 174(6):877-88 (Sep. 11, 2006).
Dorman, et al "Viral infections in interferon-gamma receptor deficiency." The Journal of Pediatrics 135(5):640-643 (Nov. 2006).
Kim H. et al., "Epidermal growth factor-dependent association of phosphatidylinositol 3-kinase with the erbB3 gene product" J Biol. Chem. 269(40): 24747-24755 (1994).
Kohler, et al "Derivation of specific antibody-producing tissue culture and tumor lines by cell fusion." Eur. J. Immunol. 6(7): 511-519 (1976).
Kostelny et al., "Formation of a Bispecific Antibody By The Use Of Leucine Zippers." J. Immunol., 148(5) 1547-1557 (1992).
Dorman, et al "Clinical features of dominant and recessive interferon gamma receptor 1 deficiencies." Lancet 364(9451): 2113-2121 (Dec. 2004).
Merrifield "Solid Phase Peptide Synthesis I, The Synthesis of a Tetrapeptide." J. Am. Chem. Soc. 85:21-49 (1962).
Milstein and Cuello "Hybrid hybridomas and their use in immunohistochemistry." Nature, 305:537-540 (1983).
Radziwill, et al "The Bcr kinase downregulates Ras signaling by phosphorylating AF-6 and binding to its PDZ domain." Mol. Cell Biol. (13): 4663-4642 (Jul. 23, 2003).
Morrison et al., "Chimeric human antibody molecules: Mouse antigen-binding domains with human constant region domains." Proc. Nat'l Acad. Sci. 81: 6851-6855 (1984).
Moses et al., "Identification of an Inhibitor of Neovascularization from cartilage." Science, 248:1408-1410 (1990).
Mullinax et al., "Identification of human antibody fragment clones specific for tetanus toxoid in a bacteriophage gamma immunoexpression library." Proc. Nat'l Acad. Sci. 87: 8095-8099 (Oct. 1990).
Nakamura, Y., "Codon usage tabulated from international DNA sequence databases: status for the year 2000." Nucleic Acids Res. 28(1): 292 (Jan. 2000).
Nardi, et al., "Mechanisms and implications of imatinib resistance mutations in BCR-ABL." Curr. Opin. Hematol. 11: 35-43 (2003).
Shackleton, et al "LMNA, encoding lamin A/C, is mutated in partial lipodystrophy." Nat. Genet. (2):153-156 (Feb. 24, 2000).
Shankaran, et al "IFN gamma and lymphocytes prevent primary tumour development and shape tumour immunogenicity." Nature 410: 1107-1111 (Apr. 26, 2001).
Feske, et al "A mutation in Orai1 causes immune deficiency by abrogating CRAC channel function." Nature 441: 179-85 (May 11, 2006).
Neuberger, et al "Recombinant antibodies possessing novel effector functions." Nature. 312(5995): 604-608 (Dec. 1984).
Newman et al., "Primatization of Recombinant Antibodies for Immunotherapy of human Diseases: A Macaque/Human Chimeric Antibody Against Human CD4." BioTechnology 10: 1455-1460 (1992).
Nissim et al., "Antibody fragments from a 'single pot' phage display library as immunochemical reagents." EMBO J. 13(3):692-698 (Feb. 1994).
Ostberg, et al.,"Human x (Mouse x Human) Hybridomas Stably Producing Human Antibodies", Hybridoma 2(4): 361-367 (1983).
Olayioye, et al.,"The ErbB signaling network: receptor heterodimerization in development and cancer", The EMBO Journal 19(13): 3159-3167 (2000).

Liu, et al., "Induction of prosurvival molecules by apoptotic stimuli: involvement of FOX03a and ROS", Oncogene 24: 2020-2031 (2005).
Order, et al., "Analysis, Results, and Future Prospective of the Therapeutic Use of Radiolabeled Antibody in Cancer Therapy", Monoclonal Antibodies for Cancer Detection and Therapy, Baldwin et al. (eds.), pp. 303-316 (Academic Press 1985).
Paweletz, et al., "Reverse phase protein microarrays which capture disease progression show activation of pro-survival pathways at the cancer invasion front", Oncogene 20: 1981-1989 (2001).
Pluckthun et al., "Antibodies from *Escherichia coli*" The Pharmacology of Monoclonal Antibodies, vol. 113, Rosenburg and Moore, eds. (Springer-Verlag: New York, 1994), pp. 269-315.
Prigent, et al., "Identification of c-erbB-3 binding sites for phosphatidylinositol 3'-kinase and SHC using an EGF receptor/c-erbB-3 chimera" The EMBO Journal 13(12): 2831-2841 (1994).
Cao, Kan "A lamin A protein isoform over expressed in Hutchinson-Gilford progeria syndrome interferes with mitosis in progeria and normal cells" Proc. Natl. Acad. Sci U S A. 104(12): 4949-4954 (Mar. 2007).
Dechat, H. "Alterations in mitosis and cell cycle progression caused by a mutant lamin A known to accelerate human aging." Proc. Natl. Acad. Sci U S A. 104(12): 4955-60 (Mar. 20, 2007).
Hanes, J. "In vitro selection and evolution of functional proteins by using ribosome display" Proc. Natl. Acad. Sci. U. S. A. 94(10): 4937-4342 (1997).
Hanes, J. "Ribosome display efficiently selects and evolves high-affinity antibodies in vitro from immune libraries." Proc. Natl. Acad. Sci. U. S. A. 95(24): 14130-14135 (1998).
Masui, et al., "A possible association between missense polymorphism of the breakpoint cluser region gene and lithium prophylaxis in bipolar disorder", Progress in Neuro-Psychopharmacogy & Biological Psychiatry 32: 204-208 (2008).
Reddy, et al., "Transcriptional repression mediated by repositioning of genes to the nuclear lamina," Nature 452: 243-247 (Mar. 13, 2008).
Rosnet, et al.,"Hematopoietic Receptors of Class III Receptor-type Tyrosine Kinases", Critical Reviews in Ontogenesis, 4(6): 595-613 (1993).
Rush, et al., "Immunoaffinity Profiling of Tyrosine Phosphorylation in Cancer Cells," Nature Biotechnology, 23(1): 94-101 (2005).
Schaller, et al.,"Autophosphorylation of the Focal Adhesion Kinase, pp125FAK Directs SH2-Dependent Binding of pp60src", Molecular and Cellular Biology, 14(3): 1680-1688 (Mar. 1994).
Schindler, et al., "Structural Mechanism for STI-571 Inhibition of Abelson Tyrosine Kinase", Science 289: 1938-1942 (2000).
Schreiber, et al., "Target-Oriented and Diversity-Oriented Organic Synthesis in Drug Discovery", Science 287, 1964-1969 (2000).
Castrillon, et al., "Suppression of Ovarian Follicle Activation in Mice by the Transcription Factor Foxo3a", Science 301: 215-218 (2003).
Shalaby, et al., "Development of Humanized Bispecitic Antibodies Reactive with Cytotoxic Lymphocytes and Tumor Cells Overexpressing the HER2 Protooncogene", J. Exp. Med., 175: 217-225 (Jan. 1992).
Shen, et al.,"Evidence for SH3 domain directed binding and phosphorylation of Sam68 by Src", Oncogene 18 4647-4653 (1999).
Spira, et al.,"The identification of monoclonal class switch variants by Sib Selection and an ELISA Assay", Journal of Immunological Methods, 74 (1984) 307-315.
Steplewski, et al., "Isolation and characterization of anti-monosialoganglioside monoclonal antibody 19-9 class-switch variants", Proc. Nat'l. Acad. Sci., USA vol. 82 pp. 8653-8657, Dec. 1985.
Stryer, et al., "Fluorescence Spectroscopy of Proteins" Science, 162: 526-533 (1986).
Suresh, et al., "Bispecific monoclonal antibodies from hybrid hybridomas" Methods in Enzymology, vol. 121, 210-228 (1986).

Tutt, et al., "Trispecific F(ab'), Derivatives That Use Cooperative Signaling Via the TCR/CD3 Complex and CD2 to Activate and Redirect Resting Cytotoxic T Cells" The Jouhnal of Immunology 147(1):60-9 (1991).
Upstate, et al., "Antibodies for Phosphorylation & Beyond", Internet Article, Jun. 2004, 1-5.
Vijapurkar, et al.,"Roles of mitogen-activated protein kinase and phoshoinositide 3'kinase in ErbB2/ErbB3 coreceptor-mediated heregulin signaling" Experimental Cell Research 284, 291-302 (2003).
Walker. et al., "Interaction of Human IgG Chimeric Antibodies With the Human FcRII Receptors: Requirements for Antibody-Mediated Host Cell-Target Cell Interaction" Molecular Immunology , vol. 26 No. 4, pp. 403-411 (1989).
Wetzel, et al., Evaluation of CML model cell lines ad imatinib mesylate response: Determinants of signaling profiles. Journal of Immunological Methods, 305: 59-66 (2005).
Yamamoto, et al., "Activating mutation of D835 within the activation loop of FLT3 in human hematologic malignancies" Blood, vol. 97, No. 8 2434-2439 (Apr. 15, 2001).
Yang, et al., "Lysine acetylation and the bromodomian: a new partnership for signaling", BioEssays, vol. 26, Iss 10, 1076-1087 (2004).
Yeatman, et at, "A Renaissance for SRC", Nature Rev. Cancer 4(6):470-480 (Jun. 2004).
Yeung, et al., "Quantitative Screening of Yeast Surface-Displayed Polypeptide Libraries by Magnetic Bead Capture" Biotechnol. Prog. 18(2):212-20 (2002).
Yokota, et al., "Internal tandem duplication of the FLT3 gene is preferentially seen in acute myeloid leukemia and myelodysplastic syndrome among various hematological malignancies. A study on a large series of patients and cell lines", Leukemia 11: 1605-1609 (1997).
Zapata, et al., "Engineering linear F (ab')2 fragments for efficient production in *Escherichia coli* and enhanced antiproliferative activity" Protein Engineering vol. 8 No. 10 pp. 1057-1062, 1995.
Zhang, et al., "Phosphoprotein Analysis Using Antibodies Broadly Reactive against Phosphorylated Motifs" Journal of Biological Chemistry, vol. 227 (42) 39379-39387 (2002).
Roof, et al., "Molecular Characterization of abLIM, a Novel Actin-binding and Double Zinc Finger Protein" Journal of Cell Biology, vol. 138 (3) 575-588 ( Aug. 11, 1997).
Mustelin, et al., "Positive and negative regulation of T-cell activation through kinases and phosphatases" Biochemical Journal, vol. 371 (1) 15-27 (Apr. 1, 2003).
Lucas, et al., "Regulation of Synthesis and Activity of the PLSTIRE Protein (Cyclin-Dependent Kinase 6 (cdk6)), a Major Cyclin D-Associated cdk4 Homologue in Normal Human T Lymphocytes" Journal of Immunology vol. 154 (12) 6275-6284 (1995).
Meyerson et al., "A family of human cdc2-related protein kinases" EMBO Journal vol. 11 (8) 2909-2917 (1992).
Nagasawa et al., "Rapid Nuclear Translocation and Increases Activity of Cyclin-Dependent Kinase 6 After T Cell Activation" Journal of Immunology vol. 158 (11) 5146-5154 (1997).
Cell Signaling Technology, "Phospho-LAT (Tyr191) Antibody" 1-3 (May 2002).
Iavarone et al., "Repression of the CDK activator Cdc25A and cell cycle arrest by cytokine TGF-beta in cells lacking the CDK inhibitor p15" Nature vol. 387 (6631) 417-422 (1997).
BD Biosciences "BC(TM) Phospho-Specific Solutioins" [online] (2003).
Lee et al., "T-Cell Receptor Signaling Precedes Immunological Synapse Function," Science 295: 1539-1542 (Feb. 22, 2002).

* cited by examiner

FIGURE 2

| | Protein Name (short) | Protein Name (full) | Accession Number | Protein Type | Phospho-Tyr Residue | Phosphorylation Site Sequence | SEQ ID NO: |
|---|---|---|---|---|---|---|---|
| 1 | abLIM | LIM actin-binding protein 1 | O14639 | Actin binding protein | 396 | IPKVKAIyDIERPDL | SEQ ID NO: 1 |
| 2 | abLIM | LIM actin-binding protein 1 | O14639 | Actin binding protein | 406 | ERPDLItyEPFYTSG | SEQ ID NO: 2 |
| 3 | abLIM | LIM actin-binding protein 1 | O14639 | Actin binding protein | 410 | LITyEPFYTSGYDDK | SEQ ID NO: 3 |
| 4 | Drebrin 1 | drebrin 1 isoform b | Q16643 | Actin binding protein | 622 | KAPPPVFvNKPPEID | SEQ ID NO: 4 |
| 5 | Drebrin F | HIP-55 | Q9UJU6 | Actin binding protein | 162 | QAPVGSVyQKTNAVS | SEQ ID NO: 5 |
| 6 | Filamin A | filamin 1 | P21333 | Actin binding protein | 1047 | PYEVEVTyDGVPVPG | SEQ ID NO: 6 |
| 7 | CASKIN2 | cask-interacting protein 2 | Q8WXE0 | Adaptor/scaffold | 384 | EPPHPLTySQLPRVG | SEQ ID NO: 7 |
| 8 | DOCK2 | dedicator of cyto-kinesis 2 | Q92608 | Adaptor/scaffold | 221 | MSKDQPDyAMYSRIS | SEQ ID NO: 8 |
| 9 | DOCK2 | dedicator of cyto-kinesis 2 | Q92608 | Adaptor/scaffold | 224 | DQPDYAMySRISSSP | SEQ ID NO: 9 |
| 10 | LIM | enigma homolog | O60705 | Adaptor/scaffold | 251 | VERYTEFyHVPTHSD | SEQ ID NO: 10 |
| 11 | NRAGE | melanoma antigen D1 | Q9Y5V3 | Adaptor/scaffold | 92 | TKGPNGVyDFSQAHN | SEQ ID NO: 11 |
| 12 | SIT | SHP2 interacting tm adaptor | Q9Y3P8 | Adaptor/scaffold | 95 | PLYGNLHyLQTGRLS | SEQ ID NO: 12 |
| 13 | LPP | Lipoma-preferred-partner | Q93052 | Adaptor/scaffold, Cytoskeletal protein | 317 | RNDSDPTyGQQGHPN | SEQ ID NO: 13 |
| 14 | Erbin | erbb2-interacting protein | Q96RT1 | Adhesion | 972 | PQSAPQIyGPPQYNI | SEQ ID NO: 14 |
| 15 | Erbin | erbb2-interacting protein | Q9H223 | Adhesion | 981 | PPQYNIQySSSAAVK | SEQ ID NO: 15 |
| 16 | Erbin | erbb2-interacting protein | Q96RT1 | Calcium-binding protein | 1107 | PEGDYLSyREFHSAG | SEQ ID NO: 16 |
| 17 | Bid | Bid | P55957 | Apoptosis | 54 | LAPQWEGyDELQTDG | SEQ ID NO: 17 |
| 18 | RCAS1 | cancer associated surface antigen | O00559 | Apoptosis | 94 | LEQLEPDyFKDMTPT | SEQ ID NO: 18 |
| 19 | BAG3 | BAG-3 | O95817 | Apoptosis, Chaperone | 247 | YQTHQPVyHKIQGDD | SEQ ID NO: 19 |
| 20 | EHD4 | EH-domain containing 4 | Q9H223 | Calcium-binding protein | 451 | VAKDKPVyDELFYTL | SEQ ID NO: 20 |
| 21 | EHD4 | EH-domain containing 4 | Q9H223 | Calcium-binding protein | 456 | PVYDELFyTLSPING | SEQ ID NO: 21 |
| 22 | SGT1 | sup. of G2 allele of SKP1 | Q9Y2Z0 | Cell cycle regulation | 285 | NRLFQQIySDGSDEV | SEQ ID NO: 22 |
| 23 | Kv-beta2 | K+ channel beta-2 | Q13303 | Channel, potassium | 25 | TGSPGMIySTRYGSP | SEQ ID NO: 23 |
| 24 | Cdc37 | CDC37 homolog | Q16543 | Chaperone | 298 | GLDPVEWyESLPEEL | SEQ ID NO: 24 |
| 25 | FKBP8 | FK506-binding protein 8 | Q14318 | Chaperone | 265 | VLAQQGEySEAIPIL | SEQ ID NO: 25 |
| 26 | HDJ2 | DNAJ-like 2 | P31689 | Chaperone | 381 | RHYNGEAyEDDEHHP | SEQ ID NO: 26 |
| 27 | STI1 | stress-induced-phoshoprot. 1 | P31948 | Chaperone | 354 | KEQERLAyINPDLAL | SEQ ID NO: 27 |
| 28 | TBCB | cytoskeleton-assoc. protein 1 | Q99426 | Chaperone, Cytoskeletal protein | 98 | SGARLGEyDVSRVE | SEQ ID NO: 28 |
| 29 | TBCB | cytoskeleton-assoc. protein 1 | Q99426 | Chaperone, Cytoskeletal protein | 114 | YTISQEAyDQRQDTV | SEQ ID NO: 29 |
| 30 | CD46 | CD46 antigen | P15529 | Cofactor | 384 | KADGGAEyATYQTKS | SEQ ID NO: 30 |
| 31 | CD46 | CD46 antigen | P15529 | Cofactor | 387 | GGAEYATyQTKSTTP | SEQ ID NO: 31 |
| 32 | CLIM1 | PDZ and LIM domain 1 | O00151 | Cytoskeletal protein | 144 | ARVTNQyNNPAGLY | SEQ ID NO: 32 |
| 33 | CLIM1 | PDZ and LIM domain 1 | O00151 | Cytoskeletal protein | 151 | YNNPAGLySSENISN | SEQ ID NO: 33 |
| 34 | EB1 | APC-binding protein EB1 | Q15691 | Cytoskeletal protein | 124 | ANYDGKDyDPVAARQ | SEQ ID NO: 34 |
| 35 | Emerin | emerin | P50402 | Cytoskeletal protein | 85 | KKEDALLyQSKGYND | SEQ ID NO: 35 |
| 36 | Emerin | emerin | P50402 | Cytoskeletal protein | 95 | KGYNDDYyEESYFTT | SEQ ID NO: 36 |
| 37 | Emerin | emerin | P50402 | Cytoskeletal protein | 99 | DDYYEESyFTTRTYG | SEQ ID NO: 37 |
| 38 | MAP1A | microtubule-assoc. protein1A | P78559 | Cytoskeletal protein | 773 | PRFHTSTyDLPGPEG | SEQ ID NO: 38 |
| 39 | NUDE1 | LIS1-interacting prot. NUDE1 | Q9NXR1 | Cytoskeletal protein | 279 | ASCRNLVyDQSPNRT | SEQ ID NO: 39 |

FIGURE 2

| | A | B | C | D | F | G | H |
|---|---|---|---|---|---|---|---|
| 41 | RP1 | APC-binding protein EB2 | Q15555 | Cytoskeletal protein | 167 | ANYDGKEyDPVEARQ | SEQ ID NO: 40 |
| 42 | tubulin, alpha-1 | tubulin, alpha | P05209 | Cytoskeletal protein | 357 | GFKVGINyQPPTVVP | SEQ ID NO: 41 |
| 43 | tubulin, beta-1 | tubulin, beta | P07437 | Cytoskeletal protein | 36 | GIDPTGTyHGDSDLQ | SEQ ID NO: 42 |
| 44 | cortactin | cortactin isoform a | Q14247 | Cytoskeletal protein, Actin binding protein | 453 | YSMEAADyREASSQQ | SEQ ID NO: 43 |
| 45 | ZNF330 | zinc finger protein 330 | Q9Y3S2 | DNA binding protein | 308 | NLNLGRTyASGYAHY | SEQ ID NO: 44 |
| 46 | ZNF330 | zinc finger protein 330 | Q9Y3S2 | DNA binding protein | 315 | YASGYAHyEEQEN | SEQ ID NO: 45 |
| 47 | Rho-GDI beta | Rho GDI 2 | P52566 | G protein regulator, misc. | 24 | ELDSKLNyKPPPQKS | SEQ ID NO: 46 |
| 48 | ARF GAP 3 | ADP-ribosylation factor GAP1 | Q9NP61 | GTPase activating protein, ARF | 349 | NDDSDDSyFTSSSSY | SEQ ID NO: 47 |
| 49 | centaurin-beta 2 | centaurin, beta 2 | Q15057 | GTPase activating protein, ARF | 750 | GQPGDETyQDIFRDF | SEQ ID NO: 48 |
| 50 | GIT2 | GIT2 protein | Q14161 | GTPase activating protein, ARF | 484 | KQATTNVyQVQTGSE | SEQ ID NO: 49 |
| 51 | GIT2 | GIT2 protein | Q14161 | GTPase activating protein, ARF | 492 | QVQTGSEyTDTSNHS | SEQ ID NO: 50 |
| 52 | PPP1R11 | prot. phosphatase 1, reg. su 11 | O60927 | Inhibitor protein | 64 | SSKCCCIyEKPRAFG | SEQ ID NO: 51 |
| 53 | PIP5K | PIP5K | Q9Y2I7 | Kinase, lipid | 1772 | LRGADSAyYQVGQTG | SEQ ID NO: 52 |
| 54 | HYD | ubiquitin protein ligase EDD | O95071 | Ligase, Ubiquitin conjugating system | 1746 | ASSAGLIyIDPSNLR | SEQ ID NO: 53 |
| 55 | endofin | endofin | Q7Z3T8 | Lipid binding protein | 219 | DTTLSDSyNYSGTEN | SEQ ID NO: 54 |
| 56 | endofin | endofin | Q7Z3T8 | Lipid binding protein | 221 | TLSDSYNySGTENLK | SEQ ID NO: 55 |
| 57 | NuMA-1 | nucl. mitotic apparatus protein | Q14980 | Nuclear, misc. | 1774 | VESLESLyFTPIPAR | SEQ ID NO: 56 |
| 58 | 1-Cys PRX | peroxiredoxin 6 | P30041 | Oxidoreductase | 88 | WSKDINAyNCEEPTE | SEQ ID NO: 57 |
| 59 | NKEF-A | peroxiredoxin 1 | Q06830 | Oxidoreductase | 194 | DVQKSKEyFSKQK | SEQ ID NO: 58 |
| 60 | FAF-X | ubiquitin-spec. protease, X-linked | Q93008 | Protease (non-proteasomal) | 2533 | GQRAQENyEGSEEVS | SEQ ID NO: 59 |
| 61 | Cdk6 | cdk6 | Q00534 | Protein kinase, Ser/Thr (non-receptor), CMGC group, CDK family, CDK4 subfamily | 13 | LCRADQQyECVAEIG | SEQ ID NO: 60 |
| 62 | Cdk6 | cdk6 | Q00534 | Protein kinase, Ser/Thr (non-receptor), CMGC group, CDK family, CDK4 subfamily | 24 | AEIGEGAyGKVFKAR | SEQ ID NO: 61 |
| 63 | SRPK2 | SR-protein-specific kinase | P78362 | Protein kinase, Ser/Thr (non-receptor), CMGC group, SRPK family, N/A subfamily | 318 | SNDQDGEyCPEVKLK | SEQ ID NO: 62 |
| 64 | ZAP70 | ZAP70 | P43403 | Protein kinase, tyrosine (non-receptor), TK group, Syk family, N/A subfamily | 248 | LKADGLIyCLKEACP | SEQ ID NO: 63 |
| 65 | PTP1B | PTP1B | P18031 | Protein phosphatase, tyrosine (non-receptor) | 20 | SGSWAAIyQDIRHEA | SEQ ID NO: 64 |
| 66 | SRPR | signal recognition particle receptor | P08240 | Receptor, misc. | 261 | ANKEVLDySTPTTNG | SEQ ID NO: 65 |
| 67 | LDLR | LDL receptor | P01130 | Receptor, protein translocating | 845 | ICHNQDGySYPSRQM | SEQ ID NO: 66 |
| 68 | TfR | transferrin receptor | P02786 | Receptor, protein translocating | 20 | FGGEPLSyTRFSLAR | SEQ ID NO: 67 |
| 69 | hnRNP 2H9 | hnRNP H3 isoform a | P31942 | RNA binding protein | 296 | GMDNQGGySVGVRMG | SEQ ID NO: 68 |
| 70 | hnRNP A0 | hnRNP A0 | Q13151 | RNA binding protein | 180 | AVPKEDIySGGGGGG | SEQ ID NO: 69 |
| 71 | hnRNP F | hnRNPF | P52597 | RNA binding protein | 246 | GYGGYEEySGLSDGY | SEQ ID NO: 70 |
| 72 | hnRNP H' | hnRNPH1 | P55795 | RNA binding protein | 246 | GYGGYDDyNGYNDGY | SEQ ID NO: 71 |
| 73 | RBM4 | RNA binding protein 4 | Q9BWF3 | RNA binding protein | 190 | VADLTEQyNEQYGAV | SEQ ID NO: 72 |

FIGURE 2

| | A | B | C | D | F | G | H |
|---|---|---|---|---|---|---|---|
| 74 | RBM4 | RNA binding protein 4 | Q9BWF3 | RNA binding protein | 194 | TEQYNEQyGAVRTPY | SEQ ID NO: 73 |
| 75 | SF3A1 | splicing factor 3a, subunit 1 | Q15459 | RNA binding protein | 456 | KQSDDEVyAPGLDIE | SEQ ID NO: 74 |
| 76 | snRNP C | snRNP C | P09234 | RNA binding protein | 8 | MPKFYCDyCDTYLTH | SEQ ID NO: 75 |
| 77 | snRNP C | snRNP C | P09234 | RNA binding protein | 12 | YCDYCDTyLTHDSPS | SEQ ID NO: 76 |
| 78 | Ets-1 | v-ets | P14921 | Transcription factor | 205 | SLKYENDyPSVILRD | SEQ ID NO: 77 |
| 79 | Ets-1 | v-ets | P14921 | Transcription factor | 223 | TDTLQNDyFAIKQEV | SEQ ID NO: 78 |
| 80 | FUBP1 | FUSE-binding protein | Q96AE4 | Transcription factor | 58 | TSLNSNDyGYGGQKR | SEQ ID NO: 79 |
| 81 | Kaiso | kaiso | O00319 | Transcription factor | 443 | ANIGEDTyDIVIPVK | SEQ ID NO: 80 |
| 82 | Max | MAX protein isoform a | P25912 | Transcription factor | 123 | PSSDNSLyTNAKGST | SEQ ID NO: 81 |
| 83 | NSBP1 | NSBP1 | P82970 | Transcription factor | 76 | EAVVEEDyNENAKNG | SEQ ID NO: 82 |
| 84 | YB-1 | Y box-binding protein I | P16991 | Transcription factor | 162 | PRNYQQNyQNSESGE | SEQ ID NO: 83 |
| 85 | ZFP 598 | zinc finger protein 598 | Q86UK7 | Transcription factor | 306 | GVVGGEDyEEVDRYS | SEQ ID NO: 84 |
| 86 | RPA40 | RNA polym. I subunit RPA40 | O15160 | Transcription initiation complex | 33 | TTDFPGNySGYDDAW | SEQ ID NO: 85 |
| 87 | AIP | AHR intereacting prot. | O00170 | Transcription, coactivator/corepressor | 248 | KLVVEEYyEVLDHCS | SEQ ID NO: 86 |
| 88 | TRIP4 | activat. signal cointegrator 1 | Q15650 | Transcription, coactivator/corepressor | 289 | VIDDESDyFASDSNQ | SEQ ID NO: 87 |
| 89 | eIF4G | translation initiation factor 4 | Q04637 | Translation initiation complex | 594 | IQPGEQKyEYKSDQW | SEQ ID NO: 88 |
| 90 | eIF4H | eIF4H1 | Q15056 | Translation initiation complex | 101 | SLKEALTyDGALLGD | SEQ ID NO: 89 |
| 91 | RPS3a | ribosomal protein S3a | P49241 | Translation initiation complex | 255 | KVERADGyEPPVQES | SEQ ID NO: 90 |
| 92 | UBE1 | ubiquitin-activat. enzyme E1 | P22314 | Ubiquitin conjugating system | 55 | ADIDEGLySRQLYYL | SEQ ID NO: 91 |
| 93 | TACC1 | transform. coiled-coil prot. | O75410 | Unknown (putative breast cancer candidate gene) | 533 | EPEEDLEyFECSNVP | SEQ ID NO: 92 |
| 94 | SCAMP3 | propin 1 | NP_005689 | Vesicle protein | 53 | TREPPPAyEPPAPAP | SEQ ID NO: 93 |
| 95 | SNAP-gamma | gamma SNAP | Q99747 | Vesicle protein | 307 | ADEEEDEySGGLC | SEQ ID NO: 94 |
| 96 | SNX12 | sorting nexin 12 | Q9UMY4 | Vesicle protein | 23 | PQDLTDAyGPPSNFL | SEQ ID NO: 95 |

SSAQLQTNYPSSDNSLpYTNAK

YENDpYPSVILRDPLQTDTLQNDpYFAIK

| Seq # | b | y | (+1) | Seq | # | b | y | (+2) |
|---|---|---|---|---|---|---|---|---|
| | | | | Y | 1 | 82.6 | 1697.3 | 27 |
| 1 | 164.2 | 3393.6 | 27 | E | 2 | 147.2 | 1615.7 | 26 |
| 2 | 293.3 | 3230.4 | 26 | N | 3 | 204.2 | 1551.1 | 25 |
| 3 | 407.4 | 3101.3 | 25 | D | 4 | 261.7 | 1494.1 | 24 |
| 4 | 522.5 | 2987.2 | 24 | Y* | 5 | 383.3 | 1436.5 | 23 |
| 5 | 765.7 | 2872.1 | 23 | P | 6 | 431.9 | 1315.0 | 22 |
| 6 | 862.8 | 2628.9 | 22 | S | 7 | 475.4 | 1266.4 | 21 |
| 7 | 949.9 | 2531.8 | 21 | V | 8 | 525.0 | 1222.9 | 20 |
| 8 | 1049.0 | 2444.7 | 20 | I | 9 | 581.6 | 1173.3 | 19 |
| 9 | 1162.2 | 2345.6 | 19 | L | 10 | 638.2 | 1116.7 | 18 |
| 10 | 1275.3 | 2232.4 | 18 | R | 11 | 716.3 | 1060.1 | 17 |
| 11 | 1431.5 | 2119.3 | 17 | D | 12 | 773.8 | 982.0 | 16 |
| 12 | 1546.6 | 1963.1 | 16 | P | 13 | 822.4 | 924.5 | 15 |
| 13 | 1643.7 | 1848.0 | 15 | L | 14 | 878.9 | 875.9 | 14 |
| 14 | 1756.9 | 1750.9 | 14 | Q | 15 | 943.0 | 819.4 | 13 |
| 15 | 1885.0 | 1637.7 | 13 | T | 16 | 993.6 | 755.3 | 12 |
| 16 | 1986.1 | 1509.6 | 12 | D | 17 | 1051.1 | 704.7 | 11 |
| 17 | 2101.2 | 1408.5 | 11 | T | 18 | 1101.7 | 647.2 | 10 |
| 18 | 2202.3 | 1293.4 | 10 | L | 19 | 1158.2 | 596.6 | 9 |
| 19 | 2315.5 | 1192.3 | 9 | Q | 20 | 1222.3 | 540.1 | 8 |
| 20 | 2443.6 | 1079.1 | 8 | N | 21 | 1279.3 | 476.0 | 7 |
| 21 | 2557.7 | 951.0 | 7 | D | 22 | 1336.9 | 418.9 | 6 |
| 22 | 2672.8 | 836.9 | 6 | Y* | 23 | 1458.5 | 361.4 | 5 |
| 23 | 2916.0 | 721.8 | 5 | F | 24 | 1532.1 | 239.8 | 4 |
| 24 | 3063.1 | 478.6 | 4 | A | 25 | 1567.6 | 166.2 | 3 |
| 25 | 3134.2 | 331.4 | 3 | I | 26 | 1624.2 | 130.7 | 2 |
| 26 | 3247.4 | 260.4 | 2 | K | 27 | 1688.3 | 74.1 | 1 |
| 27 | 3375.5 | 147.2 | 1 | | | | | |

| Seq | # | b | y | (+1) |
|---|---|---|---|---|
| A | 1 | 72.1 | --- | 9 |
| D | 2 | 187.2 | 1133.2 | 8 |
| G | 3 | 244.2 | 1062.2 | 7 |
| L | 4 | 357.4 | 947.1 | 6 |
| I | 5 | 470.5 | 890.0 | 5 |
| Y* | 6 | 713.7 | 776.9 | 4 |
| C | 7 | 873.9 | 663.7 | 3 |
| L | 8 | 987.0 | 420.5 | 2 |
| K | 9 | 1115.2 | 260.4 | 1 |
|   |   |        | 147.2 |   |

ELDALGHELPVLAPQWEGpYDELQTDGNR

```
                        SEQUENCE LISTING

<160> NUMBER OF SEQ ID NOS: 95

<210> SEQ ID NO 1
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION:  tyrosine at position 8 is
      phosphorylated.

<400> SEQUENCE: 1

Ile Pro Lys Val Lys Ala Ile Tyr Asp Ile Glu Arg Pro Asp Leu
1               5                   10                  15

<210> SEQ ID NO 2
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION:  tyrosine at position 8 is
      phosphorylated

<400> SEQUENCE: 2

Glu Arg Pro Asp Leu Ile Thr Tyr Glu Pro Phe Tyr Thr Ser Gly
1               5                   10                  15

<210> SEQ ID NO 3
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION:  tyrosine at position 8 is
      phosphorylated

<400> SEQUENCE: 3

Leu Ile Thr Tyr Glu Pro Phe Tyr Thr Ser Gly Tyr Asp Asp Lys
1               5                   10                  15

<210> SEQ ID NO 4
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION:  tyrosine at position 8 is
      phosphorylated

<400> SEQUENCE: 4

Lys Ala Pro Pro Pro Val Phe Tyr Asn Lys Pro Pro Glu Ile Asp
```

```
                1               5                   10                  15
```

<210> SEQ ID NO 5
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 5

```
Gln Ala Pro Val Gly Ser Val Tyr Gln Lys Thr Asn Ala Val Ser
1               5                   10                  15
```

<210> SEQ ID NO 6
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at posiiton 8 is
      phosphorylated

<400> SEQUENCE: 6

```
Pro Tyr Glu Val Glu Val Thr Tyr Asp Gly Val Pro Val Pro Gly
1               5                   10                  15
```

<210> SEQ ID NO 7
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 7

```
Glu Pro Pro His Pro Leu Thr Tyr Ser Gln Leu Pro Arg Val Gly
1               5                   10                  15
```

<210> SEQ ID NO 8
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 8

```
Met Ser Lys Asp Gln Pro Asp Tyr Ala Met Tyr Ser Arg Ile Ser
1               5                   10                  15
```

<210> SEQ ID NO 9
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 9

Asp Gln Pro Asp Tyr Ala Met Tyr Ser Arg Ile Ser Ser Ser Pro

```
                1               5                   10                  15
```

<210> SEQ ID NO 10
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 10

```
Val Glu Arg Tyr Thr Glu Phe Tyr His Val Pro Thr His Ser Asp
1               5                   10                  15
```

<210> SEQ ID NO 11
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 11

```
Thr Lys Gly Pro Asn Gly Val Tyr Asp Phe Ser Gln Ala His Asn
1               5                   10                  15
```

<210> SEQ ID NO 12
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 12

```
Pro Leu Tyr Gly Asn Leu His Tyr Leu Gln Thr Gly Arg Leu Ser
1               5                   10                  15
```

<210> SEQ ID NO 13
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 13

```
Arg Asn Asp Ser Asp Pro Thr Tyr Gly Gln Gln Gly His Pro Asn
1               5                   10                  15
```

<210> SEQ ID NO 14
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 14

Pro Gln Ser Ala Pro Gln Ile Tyr Gly Pro Pro Gln Tyr Asn Ile

```
                 1               5                  10                  15
```

<210> SEQ ID NO 15
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 15

```
Pro Pro Gln Tyr Asn Ile Gln Tyr Ser Ser Ser Ala Ala Val Lys
1               5                   10                  15
```

<210> SEQ ID NO 16
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 16

```
Pro Glu Gly Asp Tyr Leu Ser Tyr Arg Glu Phe His Ser Ala Gly
1               5                   10                  15
```

<210> SEQ ID NO 17
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 17

```
Leu Ala Pro Gln Trp Glu Gly Tyr Asp Glu Leu Gln Thr Asp Gly
1               5                   10                  15
```

<210> SEQ ID NO 18
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 18

```
Leu Glu Gln Leu Glu Pro Asp Tyr Phe Lys Asp Met Thr Pro Thr
1               5                   10                  15
```

<210> SEQ ID NO 19
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 19

Tyr Gln Thr His Gln Pro Val Tyr His Lys Ile Gln Gly Asp Asp

<210> SEQ ID NO 20
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 20

Val Ala Lys Asp Lys Pro Val Tyr Asp Glu Leu Phe Tyr Thr Leu
1               5                   10                  15

<210> SEQ ID NO 21
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 21

Pro Val Tyr Asp Glu Leu Phe Tyr Thr Leu Ser Pro Ile Asn Gly
1               5                   10                  15

<210> SEQ ID NO 22
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 22

Asn Arg Leu Phe Gln Gln Ile Tyr Ser Asp Gly Ser Asp Glu Val
1               5                   10                  15

<210> SEQ ID NO 23
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 23

Thr Gly Ser Pro Gly Met Ile Tyr Ser Thr Arg Tyr Gly Ser Pro
1               5                   10                  15

<210> SEQ ID NO 24
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 24

Gly Leu Asp Pro Val Glu Val Tyr Glu Ser Leu Pro Glu Glu Leu

<210> SEQ ID NO 25
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is phosphorylated

<400> SEQUENCE: 25

Val Leu Ala Gln Gln Gly Glu Tyr Ser Glu Ala Ile Pro Ile Leu
1               5                   10                  15

<210> SEQ ID NO 26
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is phosphorylated

<400> SEQUENCE: 26

Arg His Tyr Asn Gly Glu Ala Tyr Glu Asp Asp Glu His His Pro
1               5                   10                  15

<210> SEQ ID NO 27
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is phosphorylated

<400> SEQUENCE: 27

Lys Glu Gln Glu Arg Leu Ala Tyr Ile Asn Pro Asp Leu Ala Leu
1               5                   10                  15

<210> SEQ ID NO 28
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is phosphorylated

<400> SEQUENCE: 28

Ser Gly Ala Arg Leu Gly Glu Tyr Glu Asp Val Ser Arg Val Glu
1               5                   10                  15

<210> SEQ ID NO 29
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is phosphorylated

<400> SEQUENCE: 29

Tyr Thr Ile Ser Gln Glu Ala Tyr Asp Gln Arg Gln Asp Thr Val

<210> SEQ ID NO 30
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 30

Lys Ala Asp Gly Gly Ala Glu Tyr Ala Thr Tyr Gln Thr Lys Ser
1               5                   10                  15

<210> SEQ ID NO 31
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 31

Gly Gly Ala Glu Tyr Ala Thr Tyr Gln Thr Lys Ser Thr Thr Pro
1               5                   10                  15

<210> SEQ ID NO 32
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 32

Ala Arg Val Ile Thr Asn Gln Tyr Asn Asn Pro Ala Gly Leu Tyr
1               5                   10                  15

<210> SEQ ID NO 33
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 33

Tyr Asn Asn Pro Ala Gly Leu Tyr Ser Ser Glu Asn Ile Ser Asn
1               5                   10                  15

<210> SEQ ID NO 34
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 34

Ala Asn Tyr Asp Gly Lys Asp Tyr Asp Pro Val Ala Ala Arg Gln

```
1               5                   10                  15
```

<210> SEQ ID NO 35
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 35

```
Lys Lys Glu Asp Ala Leu Leu Tyr Gln Ser Lys Gly Tyr Asn Asp
1               5                   10                  15
```

<210> SEQ ID NO 36
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 36

```
Lys Gly Tyr Asn Asp Asp Tyr Tyr Glu Glu Ser Tyr Phe Thr Thr
1               5                   10                  15
```

<210> SEQ ID NO 37
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 37

```
Asp Asp Tyr Tyr Glu Glu Ser Tyr Phe Thr Thr Arg Thr Tyr Gly
1               5                   10                  15
```

<210> SEQ ID NO 38
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 38

```
Pro Arg Phe His Thr Ser Thr Tyr Asp Leu Pro Gly Pro Glu Gly
1               5                   10                  15
```

<210> SEQ ID NO 39
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 39

Ala Ser Cys Arg Asn Leu Val Tyr Asp Gln Ser Pro Asn Arg Thr

```
1               5                   10                  15
```

<210> SEQ ID NO 40
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 40

```
Ala Asn Tyr Asp Gly Lys Glu Tyr Asp Pro Val Glu Ala Arg Gln
1               5                   10                  15
```

<210> SEQ ID NO 41
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 41

```
Gly Phe Lys Val Gly Ile Asn Tyr Gln Pro Pro Thr Val Val Pro
1               5                   10                  15
```

<210> SEQ ID NO 42
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 42

```
Gly Ile Asp Pro Thr Gly Thr Tyr His Gly Asp Ser Asp Leu Gln
1               5                   10                  15
```

<210> SEQ ID NO 43
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 43

```
Tyr Ser Met Glu Ala Ala Asp Tyr Arg Glu Ala Ser Ser Gln Gln
1               5                   10                  15
```

<210> SEQ ID NO 44
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 44

```
Asn Leu Asn Leu Gly Arg Thr Tyr Ala Ser Gly Tyr Ala His Tyr
```

```
<210> SEQ ID NO 45
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 45

Tyr Ala Ser Gly Tyr Ala His Tyr Glu Glu Gln Glu Asn
1               5                   10

<210> SEQ ID NO 46
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 46

Glu Leu Asp Ser Lys Leu Asn Tyr Lys Pro Pro Pro Gln Lys Ser
1               5                   10                  15

<210> SEQ ID NO 47
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 47

Asn Asp Asp Ser Asp Asp Ser Tyr Phe Thr Ser Ser Ser Ser Tyr
1               5                   10                  15

<210> SEQ ID NO 48
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 48

Gly Gln Pro Gly Asp Glu Thr Tyr Gln Asp Ile Phe Arg Asp Phe
1               5                   10                  15

<210> SEQ ID NO 49
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 49

Lys Gln Ala Thr Thr Asn Val Tyr Gln Val Gln Thr Gly Ser Glu
```

```
                1               5                   10                  15
```

<210> SEQ ID NO 50
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 50

```
Gln Val Gln Thr Gly Ser Glu Tyr Thr Asp Thr Ser Asn His Ser
1               5                   10                  15
```

<210> SEQ ID NO 51
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 51

```
Ser Ser Lys Cys Cys Cys Ile Tyr Glu Lys Pro Arg Ala Phe Gly
1               5                   10                  15
```

<210> SEQ ID NO 52
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 52

```
Leu Arg Gly Ala Asp Ser Ala Tyr Tyr Gln Val Gly Gln Thr Gly
1               5                   10                  15
```

<210> SEQ ID NO 53
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 53

```
Ala Ser Ser Ala Gly Leu Ile Tyr Ile Asp Pro Ser Asn Leu Arg
1               5                   10                  15
```

<210> SEQ ID NO 54
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 54

```
Asp Thr Thr Leu Ser Asp Ser Tyr Asn Tyr Ser Gly Thr Glu Asn
```

```
1               5                   10                  15
```

<210> SEQ ID NO 55
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 55

```
Thr Leu Ser Asp Ser Tyr Asn Tyr Ser Gly Thr Glu Asn Leu Lys
1               5                   10                  15
```

<210> SEQ ID NO 56
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 56

```
Val Glu Ser Leu Glu Ser Leu Tyr Phe Thr Pro Ile Pro Ala Arg
1               5                   10                  15
```

<210> SEQ ID NO 57
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 57

```
Trp Ser Lys Asp Ile Asn Ala Tyr Asn Cys Glu Glu Pro Thr Glu
1               5                   10                  15
```

<210> SEQ ID NO 58
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 58

```
Asp Val Gln Lys Ser Lys Glu Tyr Phe Ser Lys Gln Lys
1               5                   10
```

<210> SEQ ID NO 59
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 59

```
Gly Gln Arg Ala Gln Glu Asn Tyr Glu Gly Ser Glu Glu Val Ser
```

```
                    1               5                   10                  15

<210> SEQ ID NO 60
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION:  tyrosine at position 8 is
      phosphorylated

<400> SEQUENCE: 60

Leu Cys Arg Ala Asp Gln Gln Tyr Glu Cys Val Ala Glu Ile Gly
1               5                   10                  15

<210> SEQ ID NO 61
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION:  tyrosine at position 8 is
      phosphorylated

<400> SEQUENCE: 61

Ala Glu Ile Gly Glu Gly Ala Tyr Gly Lys Val Phe Lys Ala Arg
1               5                   10                  15

<210> SEQ ID NO 62
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION:  tyrosine at position 8 is
      phosphorylated

<400> SEQUENCE: 62

Ser Asn Asp Gln Asp Gly Glu Tyr Cys Pro Glu Val Lys Leu Lys
1               5                   10                  15

<210> SEQ ID NO 63
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION:  tyrosine at position 8 is
      phosphorylated

<400> SEQUENCE: 63

Leu Lys Ala Asp Gly Leu Ile Tyr Cys Leu Lys Glu Ala Cys Pro
1               5                   10                  15

<210> SEQ ID NO 64
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION:  tyrosine at position 8 is
      phosphorylated

<400> SEQUENCE: 64

Ser Gly Ser Trp Ala Ala Ile Tyr Gln Asp Ile Arg His Glu Ala
```

```
<210> SEQ ID NO 65
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 65

Ala Asn Lys Glu Val Leu Asp Tyr Ser Thr Pro Thr Thr Asn Gly
1               5                   10                  15

<210> SEQ ID NO 66
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 66

Ile Cys His Asn Gln Asp Gly Tyr Ser Tyr Pro Ser Arg Gln Met
1               5                   10                  15

<210> SEQ ID NO 67
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 67

Phe Gly Gly Glu Pro Leu Ser Tyr Thr Arg Phe Ser Leu Ala Arg
1               5                   10                  15

<210> SEQ ID NO 68
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 68

Gly Met Asp Asn Gln Gly Gly Tyr Gly Ser Val Gly Arg Met Gly
1               5                   10                  15

<210> SEQ ID NO 69
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 69

Ala Val Pro Lys Glu Asp Ile Tyr Ser Gly Gly Gly Gly Gly Gly
```

-continued

<210> SEQ ID NO 70
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 70

Gly Tyr Gly Gly Tyr Glu Glu Tyr Ser Gly Leu Ser Asp Gly Tyr
1               5                   10                  15

<210> SEQ ID NO 71
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 71

Gly Tyr Gly Gly Tyr Asp Asp Tyr Asn Gly Tyr Asn Asp Gly Tyr
1               5                   10                  15

<210> SEQ ID NO 72
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 72

Val Ala Asp Leu Thr Glu Gln Tyr Asn Glu Gln Tyr Gly Ala Val
1               5                   10                  15

<210> SEQ ID NO 73
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 73

Thr Glu Gln Tyr Asn Glu Gln Tyr Gly Ala Val Arg Thr Pro Tyr
1               5                   10                  15

<210> SEQ ID NO 74
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 74

Lys Gln Ser Asp Asp Glu Val Tyr Ala Pro Gly Leu Asp Ile Glu

```
                 1               5                  10                  15
```

```
<210> SEQ ID NO 75
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 75

Met Pro Lys Phe Tyr Cys Asp Tyr Cys Asp Thr Tyr Leu Thr His
 1               5                  10                  15

<210> SEQ ID NO 76
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 76

Tyr Cys Asp Tyr Cys Asp Thr Tyr Leu Thr His Asp Ser Pro Ser
 1               5                  10                  15

<210> SEQ ID NO 77
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 77

Ser Leu Lys Tyr Glu Asn Asp Tyr Pro Ser Val Ile Leu Arg Asp
 1               5                  10                  15

<210> SEQ ID NO 78
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 78

Thr Asp Thr Leu Gln Asn Asp Tyr Phe Ala Ile Lys Gln Glu Val
 1               5                  10                  15

<210> SEQ ID NO 79
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 79

Thr Ser Leu Asn Ser Asn Asp Tyr Gly Tyr Gly Gly Gln Lys Arg
```

```
                   1               5                  10                  15

<210> SEQ ID NO 80
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 80

Ala Asn Ile Gly Glu Asp Thr Tyr Asp Ile Val Ile Pro Val Lys
1               5                  10                  15

<210> SEQ ID NO 81
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 81

Pro Ser Ser Asp Asn Ser Leu Tyr Thr Asn Ala Lys Gly Ser Thr
1               5                  10                  15

<210> SEQ ID NO 82
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 82

Glu Ala Val Val Glu Glu Asp Tyr Asn Glu Asn Ala Lys Asn Gly
1               5                  10                  15

<210> SEQ ID NO 83
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 83

Glu Ala Val Val Glu Glu Asp Tyr Asn Glu Asn Ala Lys Asn Gly
1               5                  10                  15

<210> SEQ ID NO 84
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 84

Gly Val Val Gly Gly Glu Asp Tyr Glu Glu Val Asp Arg Tyr Ser
```

```
<210> SEQ ID NO 85
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 85

Thr Thr Asp Phe Pro Gly Asn Tyr Ser Gly Tyr Asp Asp Ala Trp
1               5                   10                  15

<210> SEQ ID NO 86
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 86

Lys Leu Val Val Glu Glu Tyr Tyr Glu Val Leu Asp His Cys Ser
1               5                   10                  15

<210> SEQ ID NO 87
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 87

Val Ile Asp Asp Glu Ser Asp Tyr Phe Ala Ser Asp Ser Asn Gln
1               5                   10                  15

<210> SEQ ID NO 88
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 88

Ile Gln Pro Gly Glu Gln Lys Tyr Glu Tyr Lys Ser Asp Gln Trp
1               5                   10                  15

<210> SEQ ID NO 89
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION: tyrosine at position 8 is
      phosphorylated

<400> SEQUENCE: 89

Ser Leu Lys Glu Ala Leu Thr Tyr Asp Gly Ala Leu Leu Gly Asp
```

```
                 1               5                  10                  15

<210> SEQ ID NO 90
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION:  tyrosine at position 8 is
      phosphorylated

<400> SEQUENCE: 90

Lys Val Glu Arg Ala Asp Gly Tyr Glu Pro Pro Val Gln Glu Ser
1               5                   10                  15

<210> SEQ ID NO 91
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION:  tyrosine at position 8 is
      phosphorylated

<400> SEQUENCE: 91

Ala Asp Ile Asp Glu Gly Leu Tyr Ser Arg Gln Leu Tyr Val Leu
1               5                   10                  15

<210> SEQ ID NO 92
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION:  tyrosine at position 8 is
      phosphorylated

<400> SEQUENCE: 92

Glu Pro Glu Glu Asp Leu Glu Tyr Phe Glu Cys Ser Asn Val Pro
1               5                   10                  15

<210> SEQ ID NO 93
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION:  tyrosine at position 8 is
      phosphorylated

<400> SEQUENCE: 93

Thr Arg Glu Pro Pro Pro Ala Tyr Glu Pro Pro Ala Pro Ala Pro
1               5                   10                  15

<210> SEQ ID NO 94
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION:  tyrosine at position 8 is
      phosphorylated

<400> SEQUENCE: 94

Ala Asp Glu Glu Glu Asp Glu Tyr Ser Gly Gly Leu Cys
```

-continued

```
<210> SEQ ID NO 95
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION:  tyrosine located at position
      8 is phosphorylated

<400> SEQUENCE: 95

Pro Gln Asp Leu Thr Asp Ala Tyr Gly Pro Pro Ser Asn Phe Leu
1               5                   10                  15
```

US 7,935,790 B2

REAGENTS FOR THE DETECTION OF PROTEIN PHOSPHORYLATION IN T-CELL RECEPTOR SIGNALING PATHWAYS

RELATED APPLICATIONS

This application is a continuation of PCT/US04/32511 filed Oct. 4, 2004 (expired).

FIELD OF THE INVENTION

The invention relates generally to antibodies and peptide reagents for the detection of protein phosphorylation, and to protein phosphorylation in cancer.

BACKGROUND OF THE INVENTION

The activation of proteins by post-translational modification represents an important cellular mechanism for regulating most aspects of biological organization and control, including growth, development, homeostasis, and cellular communication. For example, protein phosphorylation plays a critical role in the etiology of many pathological conditions and diseases, including cancer, developmental disorders, autoimmune diseases, and diabetes, as well as in proper immune function. In spite of the importance of protein modification, it is not yet well understood at the molecular level. The reasons for this lack of understanding are, first, that the cellular modification system is extraordinarily complex, and second, that the technology necessary to unravel its complexity has not yet been fully developed.

The complexity of protein modification, including phosphorylation, on a proteome-wide scale derives from three factors: the large number of modifying proteins, e.g. kinases, encoded in the genome, the much larger number of sites on substrate proteins that are modified by these enzymes, and the dynamic nature of protein expression during growth, development, disease states, and aging. The human genome encodes, for example, over 520 different protein kinases, making them the most abundant class of enzymes known. See Hunter, Nature 411: 355-65 (2001). Each of these kinases phosphorylates specific serine, threonine, or tyrosine residues located within distinct amino acid sequences, or motifs, contained within different protein substrates. Most kinases phosphorylate many different proteins: it is estimated that one-third of all proteins encoded by the human genome are phosphorylated, and many are phosphorylated at multiple sites by different kinases. See Graves et al., Pharmacol. Ther. 82: 111-21 (1999).

Many of these phosphorylation sites regulate critical biological processes and may prove to be important diagnostic or therapeutic targets for molecular medicine. For example, of the more than 100 dominant oncogenes identified to date, 46 are protein kinases. See Hunter, supra. Oncogenic kinases such as ErbB2 and Jak3, widely expressed in breast tumors and various leukemias, respectively, transform cells to the oncogenic phenotype at least in part because of their ability to phosphorylate cellular proteins. Understanding which proteins are modified by these kinases will greatly expand our understanding of the molecular mechanisms underlying oncogenic transformation. Thus, the ability to identify modification sites, e.g. phosphorylation sites, on a wide variety of cellular proteins is crucially important to understanding the key signaling proteins and pathways implicated in disease progression, as well as critical biological processes such as the immune response.

The efficient identification of protein phosphorylation sites relevant to signal transduction has been aided by the recent development of a powerful new class of antibodies, called motif-specific, context-independent antibodies, which are capable of specifically binding short, recurring signaling motifs comprising one or more modified (e.g. phosphorylated) amino acids in many different proteins in which the motif recurs. See U.S. Pat. No. 6,441,140, Comb et al. Many of these powerful new antibodies are now available commercially. See Cell Signaling Technology, Inc. 2003-04 Catalogue. More recently, a powerful new method for employing such motif-specific antibodies in immunoaffinity techniques coupled with mass spectrometric analysis to rapidly identify modified peptides from complex biological mixtures has been described. See U.S. Patent Publication No. 20030044848, Rush et al.). Such techniques will enable the rapid elucidation of protein activation and phosphorylation events underlying diseases, like cancer, that are driven by disruptions in signal transduction, as well as those underlying critical biological processes such as the immune response.

The transmission of intracellular signaling resulting from binding of the T-lymphocyte receptor (T-cell receptor) to foreign antigen presented with the major histocompatability complex (MHC) on antigen presenting cells (APCs) is a process critical to the generation of a proper immune response in mammals. Antigen-specific T-cell binding via the T-cell receptor results in a kinase-mediated signaling cascade leading to cell-specific proliferation of the activated T-cells, and their participation in the immune response against foreign antigens and cells. Defects in T-cell signaling have been associated with T-cell acute lymphocytic leukemias. See Blume-Jensen et al., Nature 411: 355-365 (2001) (describing T cell receptor beta gene translocation next to the gene encoding the Lck tyrosine kinase gene, resulting in presumably constitutive activation of Lck).

T-cell receptor-induced signaling is mediated through a variety of second messengers, protein kinases and phosphatases, and other enzymes and intermediates. It is now known that binding of the human T-cell receptor to specific antigen-MHC complex results in the activation and/or recruitment of the Src-family kinases, Lck and Fyn, which in turn phosphorylate two critical tyrosine residues within the immunoreceptor tyrosine-based activation motifs (ITAMs) in the TCR-ζ invariant chain of the TCR complex. See, e.g. Mustelin et al., Biochem J. 371: 15-27 (2003); Pitcher et al., Trends in Immunol., 24: 554-560 (2003). This process may also involve the exclusion of protein tyrosine phosphatases that would down-regulate Lck and Fyn, as well as the exclusion of Csk kinase, which negatively regulates Lck and Fyn by phosphorylation at a conserved C-terminal tyrosine (Tyr505 in Lck and Try528 in Fyn). See Mustelin et al., supra.

Phosphorylation of the ITAMs renders them high-affinity ligands for the ZAP-70 kinase, which is selectively recruited to the activated receptor complex, and (along with the kinase Syk) is subsequently activated by phosphorylation at tyrosine 493 (Tyr493) by Lck kinase. See Mustelin et al., Pitcher et al., supra. Following its activation, ZAP-70, along with Syk, in turn phosphorylates other key downstream adaptor proteins (such as LAT) and effector proteins (such as SLP-76). Further, certain phosphorylated tyrosine sites in activated ZAP-70 provide key docking sites for SH-2 domain-containing effector proteins like Lck and Cbl, which participate in a complex cascade—involving $Ca^{2+}/InsP_3$, Ras/Raf/ERK and RhoA pathways, ultimately leading to gene regulation and cell proliferation. See Mustelin et al., Pitcher et al., supra.

Although some of the signaling proteins and phosphorylation sites involved in proper T-cell receptor signaling have been identified, a clear picture of the precise proteins and phosphorylation sites involved in propagating this essential biological signal remains to be developed. For example, SHP1 phosphatase and Fyn kinase may be involved in the signaling cascade, but their precise role and substrates are unknown. See Mustelin et al., supra. Other Src-family protein tyrosine kinases, including the Tec-related kinases, Itk/Emt and Txk/Rlk, appear to be involved as well, but their precise role and substrates remains to be determined. Accordingly, the small number of T-cell receptor signaling pathway-related phosphorylation sites that have been identified to date do not facilitate a complete and accurate understanding of how this important biological signal is propagated. Indeed, it has recently been concluded that a major remaining challenge in T-cell biology is more precisely define the contribution of particular signaling molecules involved in the T-cell signaling, and to better understand the interplay between signaling molecules and pathways involved. See Mustelin et al., supra.

Accordingly, there is a continuing need to unravel the molecular mechanisms of T-cell receptor signaling by identifying the downstream signaling proteins mediating the cascade leading to proliferation of activated T-cells and their participation in the immune response. Identifying particular phosphorylation sites on such signaling proteins and providing new reagents, such as phospho-specific antibodies and AQUA peptides, to detect and quantify them remains particularly important to advancing our understanding of the biology of the critical T-cell signaling process. In turn, such advances would lead to a better understanding of diseases, such as T-cell acute lymphocytic leukemias, involving aberrant T cell signaling. See Blume-Jensen et al., supra.

SUMMARY OF THE INVENTION

The invention discloses 95 novel phosphorylation sites identified in signal transduction proteins and pathways involved in T-cell receptor signaling, and provides new reagents, including phosphorylation-site specific antibodies and AQUA peptides, for the selective detection and quantification of these phosphorylated sites/proteins. Also provided are methods of using the reagents of the invention for the detection and quantification of the disclosed phosphorylation sites.

BRIEF DESCRIPTION OF THE DRAWINGS

FIG. 2—Is a table (corresponding to Table 1) enumerating the T-cell receptor signaling protein phosphorylation sites disclosed herein: Column A=the abbreviated name of the parent protein; Column B=the full name of the parent protein; Column C=the SwissProt accession number for the protein (human sequence); Column D=the protein type/classification; Column F=the residue (in the parent protein amino acid sequence) at which phosphorylation occurs within the phosphorylation site; and Column G=the phosphorylation site sequence encompassing the phosphorylatable residue; (tyrosine residue at which phosphorylation occurs (and corresponding to the respective entry in Column F) is indicated by lowercase "y".

DETAILED DESCRIPTION OF THE INVENTION

Figure 1:
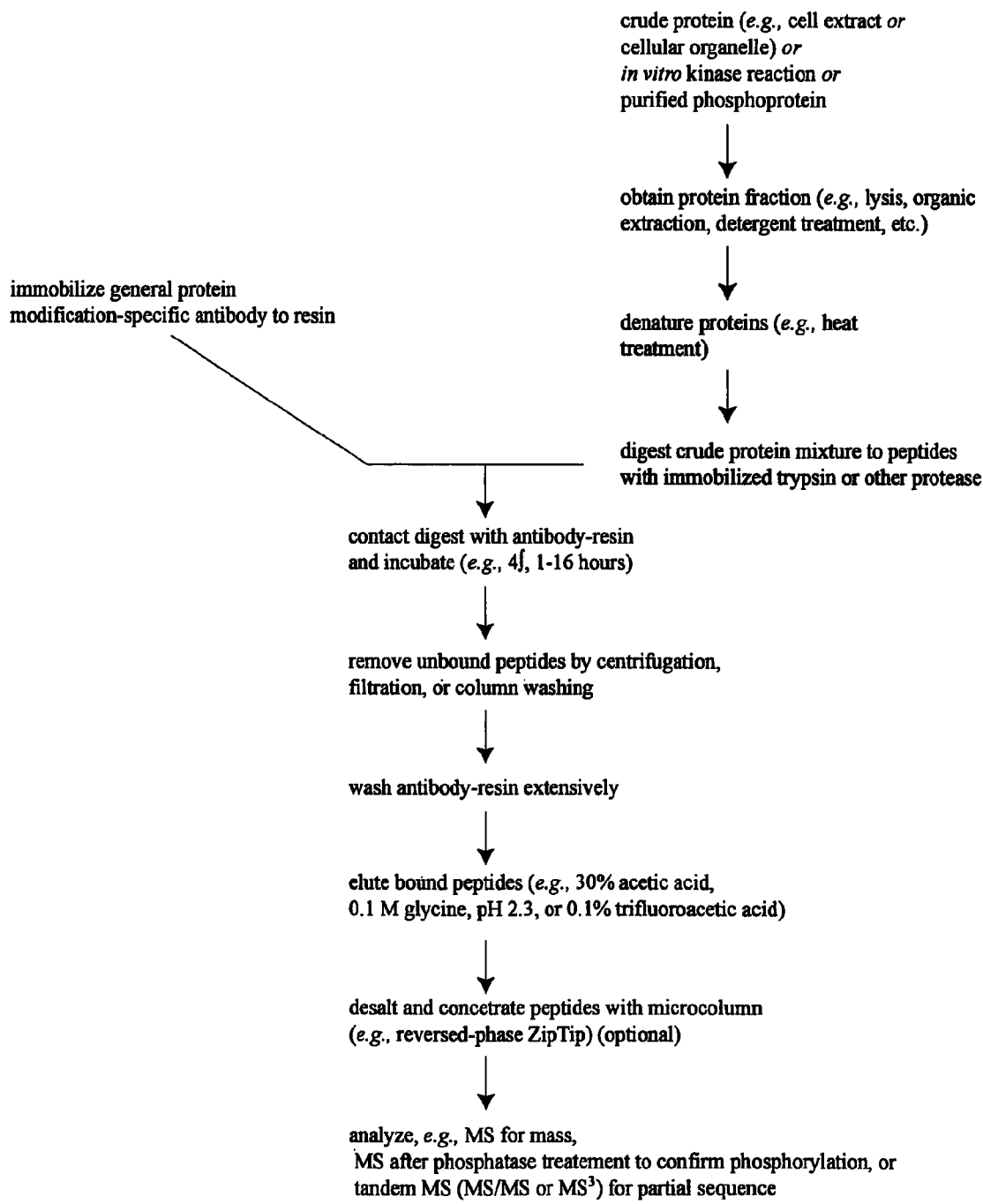
FIG. 1—Is a diagram broadly depicting the immunoaffinity isolation and mass-spectrometric characterization methodology (IAP) employed to identify the novel phosphorylation sites disclosed herein.
Figure 3:
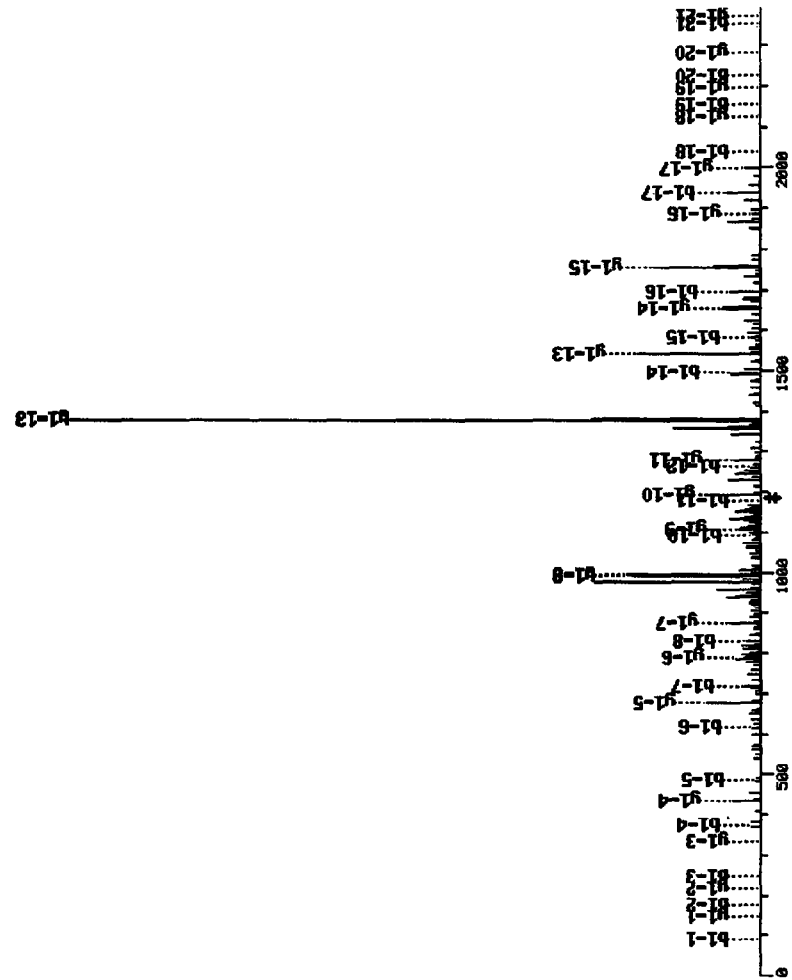
FIG. 3—is an exemplary mass spectrograph depicting the detection of the tyrosine 123 phosphorylation site in Max (see Row 82 in FIG. 2/Table 1), as further described in Example 1 (red and blue indicate ions detected in MS/MS spectrum). The asterisk indicates the novel phosphotyrosine residue identified.
Figure 4:
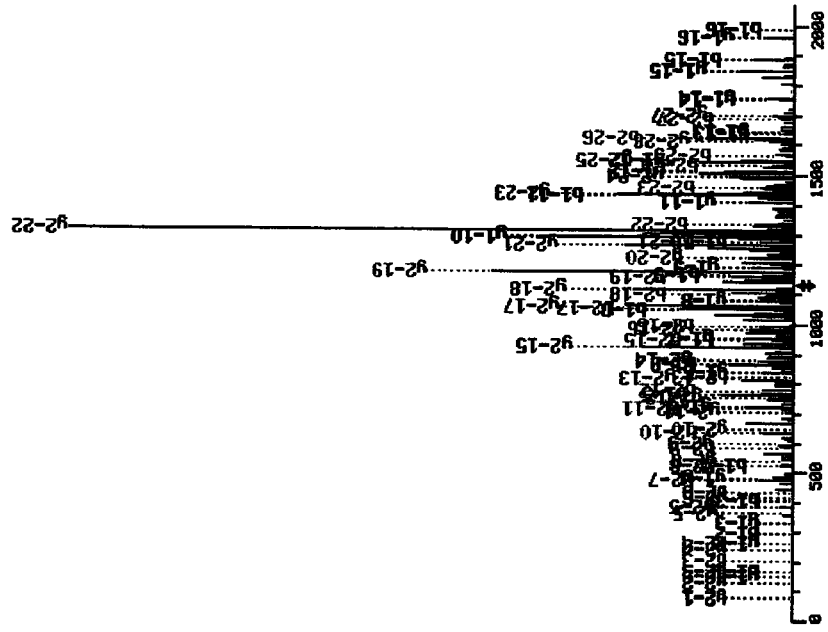
FIG. 4—is an exemplary mass spectrograph depicting the detection of the tyrosine 205 phosphorylation site in ETS-1 (see Row 78 in FIG. 2/Table 1), as further described in Example 1 (red and blue indicate ions detected in MS/MS spectrum). The asterisk indicates the novel phosphotyrosine residue identified.
Figure 5:
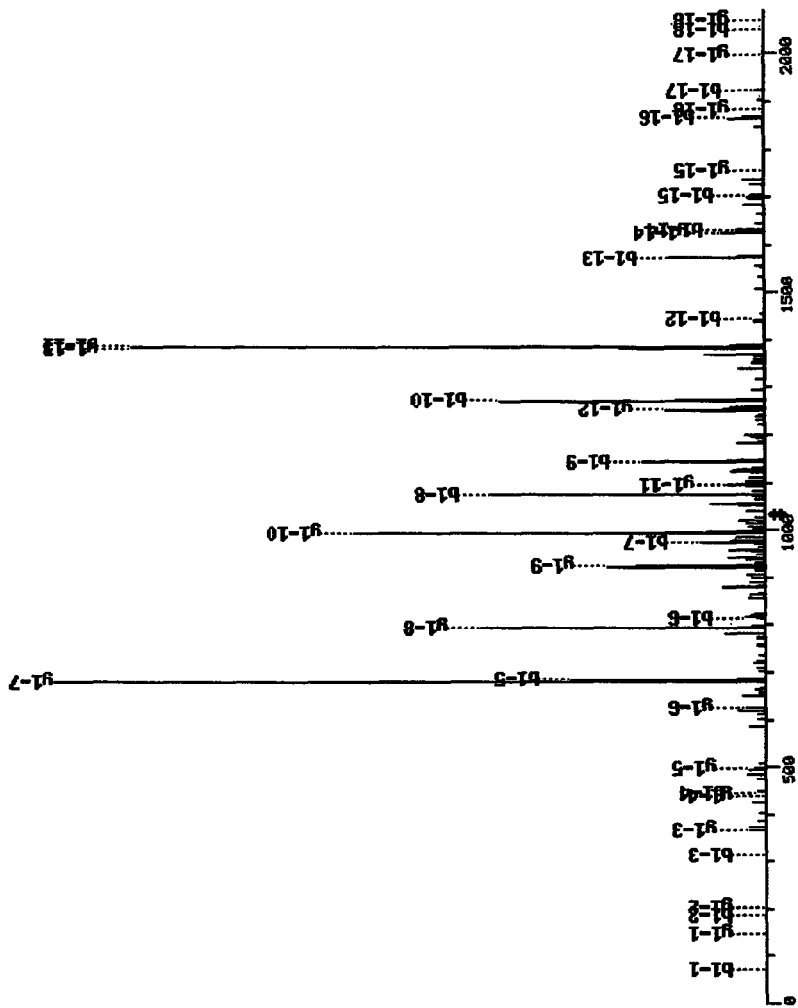
FIG. 5—is an exemplary mass spectrograph depicting the detection of the tyrosine 13 phosphorylation site in CDK6 (see Row 61 in FIG. 2/Table 1), as further described in Example 1 (red and blue indicate ions detected in MS/MS spectrum). The asterisk indicates the novel phosphotyrosine residue identified.
Figure 6:
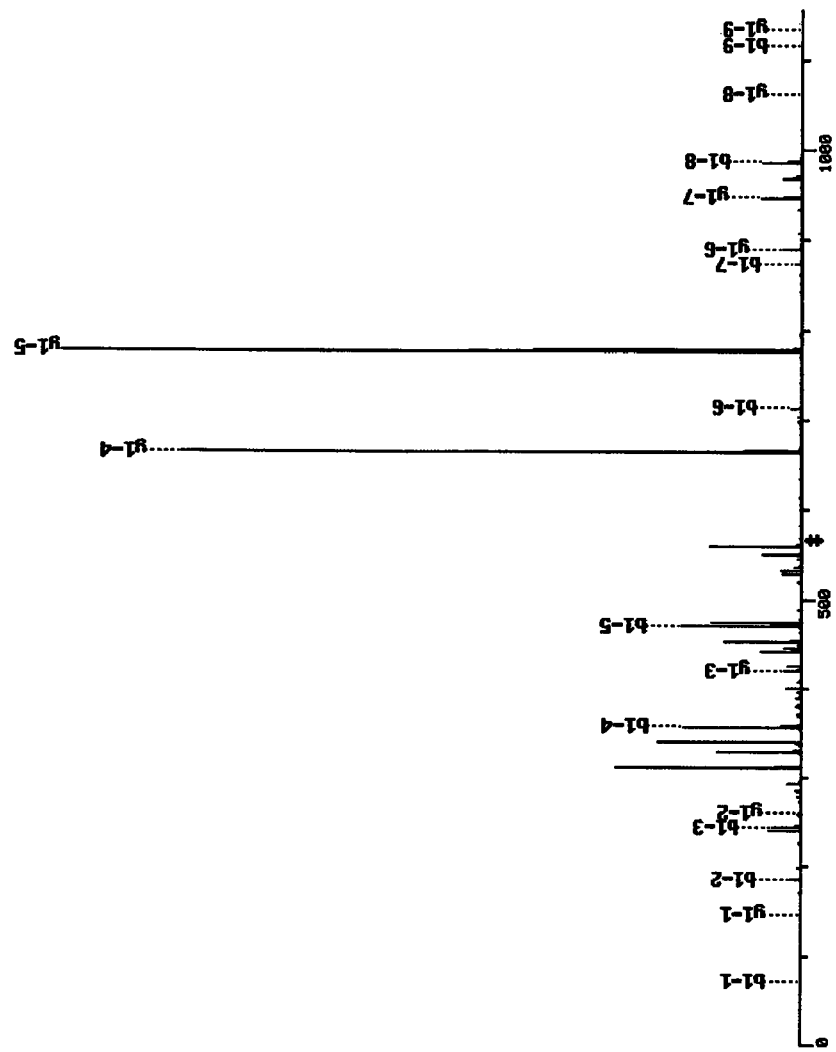
FIG. 6—is an exemplary mass spectrograph depicting the detection of the tyrosine 248 phosphorylation site in ZAP70 (see Row 64 in FIG. 2/Table 1), as further described in Example 1 (red and blue indicate ions detected in MS/MS spectrum). The asterisk indicates the novel phosphotyrosine residue identified.
Figure 7:
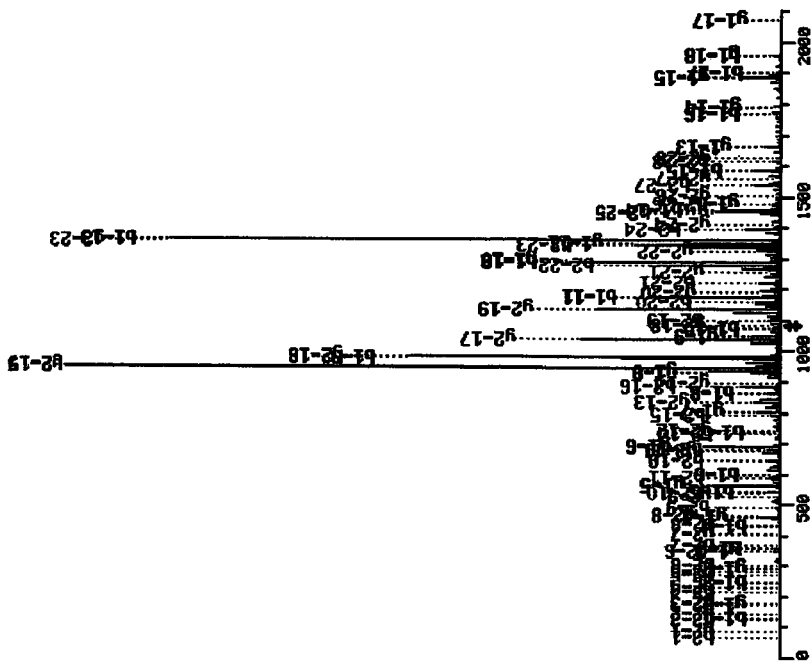
FIG. 7—is an exemplary mass spectrograph depicting the detection of the tyrosine 54 phosphorylation site in Bid (see Row 18 in FIG. 2/Table 1), as further described in Example 1 (red and blue indicate ions detected in MS/MS spectrum). The asterisk indicates the novel phosphotyrosine residue identified.

In accordance with the present invention, 95 novel protein phosphorylation sites in signaling proteins and pathways involved in T-cell receptor signaling have now been discovered. These newly described phosphorylation sites were identified by employing the techniques described in "Immunoaffinity Isolation of Modified Peptides From Complex Mixtures," U.S. Patent Publication No. 20030044848, Rush et al., using cellular extracts from an established cell line, derived from human lymphoblastic leukemia and non-Hodgkin lymphoma, in which T-cell signaling is activated, as further described below. The novel phosphorylation sites, and their corresponding parent proteins, disclosed herein are listed in Table I. These phosphorylation sites correspond to numerous different parent proteins (the full sequences of which (human) are all publicly available in SwissProt database and their Accession numbers listed in Column C of Table 1/FIG. 2), each of which fall into discrete protein type groups, for example Adaptor/Scaffold proteins, Chaperone proteins, Protein Kinases, and RNA Binding proteins, etc. (see Column D of Table 1), the phosphorylation of which is relevant to T-cell receptor signal transduction activity, as disclosed herein.

The discovery of the 95 novel protein phosphorylation sites described herein enables the production, by standard methods, of new reagents, such as phosphorylation site-specific antibodies and AQUA peptides (heavy-isotope labeled peptides), capable of specifically detecting and/or quantifying these phosphorylated sites/proteins. Such reagents are highly useful, inter alia, for studying signal transduction events underlying the progression of diseases, such as acute lymphocytic leukemias, that may involve aberrant T-cell receptor signaling. Accordingly, the invention provides novel reagents—phospho-specific antibodies and AQUA peptides—for the specific detection and/or quantification of a T-cell receptor signaling protein/polypeptide only when phosphorylated (or only when not phosphorylated) at a particular phosphorylation site disclosed herein. The invention also provides methods of detecting and/or quantifying one or more phosphorylated T-cell receptor signaling proteins using the phosphorylation-site specific antibodies and AQUA peptides of the invention.

In part, the invention provides an isolated phosphorylation site-specific antibody that specifically binds a given T-cell receptor signaling protein only when phosphorylated (or not phosphorylated, respectively) at a particular tyrosine enumerated in Column F of Table 1/FIG. 2 comprised within the phosphorylatable peptide site sequence enumerated in corresponding Column G. In further part, the invention provides a heavy-isotope labeled peptide (AQUA peptide) for the quantification of a given T-cell receptor signaling protein, the labeled peptide comprising a particular phosphorylatable peptide site/sequence enumerated in Column G of Table 1/FIG. 2 herein. For example, among the reagents provided by the invention is an isolated phosphorylation site-specific antibody that specifically binds the Cdk6 kinase (serine/threonine) only when phosphorylated (or only when not phosphorylated) at tyrosine 13 (see Row 61 (and Columns F and G) of Table 1/FIG. 2). By way of further example, among the group of reagents provided by the invention is an AQUA peptide for the quantification of phosphorylated Cdk6 kinase, the AQUA peptide comprising the phosphorylatable peptide sequence listed in Column G, Row 61, of Table 1/FIG. 2.

In one embodiment, the invention provides an isolated phosphorylation site-specific antibody that specifically binds a human T-cell receptor signaling protein selected from Column A of Table 1 only when phosphorylated at the tyrosine listed in corresponding Column F of Table 1, comprised within the peptide sequence listed in corresponding Column G of Table 1 (SEQ ID NOs: 1-95), wherein said antibody does not bind said signaling protein when not phosphorylated at said tyrosine. In another embodiment, the invention provides an isolated phosphorylation site-specific antibody that specifically binds a T-cell receptor signaling protein selected from Column A of Table 1 only when not phosphorylated at the tyrosine listed in corresponding Column F of Table 1, comprised within the peptide sequence listed in corresponding Column G of Table 1 (SEQ ID NOs: 1-95), wherein said antibody does not bind said signaling protein when phosphorylated at said tyrosine. Such reagents enable the specific detection of phosphorylation (or non-phosphorylation) of a novel phosphorylatable site disclosed herein. The invention further provides immortalized cell lines producing such antibodies. In one preferred embodiment, the immortalized cell line is a rabbit or mouse hybridoma.

In another embodiment, the invention provides a heavy-isotope labeled peptide (AQUA peptide) for the quantification of a T-cell receptor signaling protein selected from Column A of Table 1, said labeled peptide comprising the phosphorylatable peptide sequence listed in corresponding Column G of Table 1 (SEQ ID NOs: 1-95), which sequence comprises the phosphorylatable tyrosine listed in corresponding Column F of Table 1. In certain preferred embodiments, the phosphorylatable tyrosine within the labeled peptide is phosphorylated, while in other preferred embodiments, the phosphorylatable tyrosine within the labeled peptide is not phosphorylated.

Reagents (antibodies and AQUA peptides) provided by the invention may conveniently be grouped by the type of T-cell receptor signaling protein in which a given phosphorylation site (for which reagents are provided) occurs. The protein types for each respective protein (in which a phosphorylation site has been discovered) are provided in Column D of Table 1/FIG. 2, and include: Actin Binding proteins, Adaptor/Scaffold proteins, Adhesion proteins, Calcium-binding proteins, Cell Cycle Regulation or Channel proteins, Chaperones, Cofactor proteins, Cytoskeletal proteins, DNA Binding proteins, G protein or GTPase Activating proteins, Ligases, Lipid Kinases and Binding proteins, Oxidoreductases, Protein Kinases, Protein Phosphatases, Receptor proteins, RNA Binding proteins, Transcription Factor/Initiation Complex/Coactivator proteins, Translation Initiation Complex proteins, Ubitquitin Conjugating System proteins, and Vesicle proteins. Each of these distinct protein groups is considered a preferred subset of T-cell receptor signal transduction protein phosphorylation sites disclosed herein, and reagents for their detection/quantification may be considered a preferred subset of reagents provided by the invention.

Particularly preferred subsets of the phosphorylation sites (and their corresponding proteins) disclosed herein are those occurring on the following protein types/groups listed in Column D of Table 1/FIG. 2: Adaptor/Scaffold proteins, Actin Binding proteins, Adaptor/Scaffold proteins, Cytoskeletal proteins, G Protein Regulator/GTPase Activating proteins, Protein kinases, Receptor proteins, RNA Binding proteins, Transcription Factor/Initiation Complex proteins, Transcription Coactivator/Corepressor proteins, and Translation Initiation Complex proteins. Accordingly, among preferred subsets of reagents provided by the invention are isolated antibodies and AQUA peptides useful for the detection and/or quantification of the foregoing preferred protein/phosphorylation site subsets, as well as for the following preferred protein phosphorylation sites: Bid (Y54), RCAS1 (Y94), Cdc37 (Y298), PIP5K (Y1772), HYD (Y1746), FAF-X (Y2533), and UBE1 (Y55).

In one subset of preferred embodiments, there is provided:
(i) An isolated phosphorylation site-specific antibody that specifically binds a Protein Kinase selected from Column A, Rows 61-64, of Table 1 only when phosphorylated at the tyrosine listed in corresponding Column F, Rows 61-64, of Table 1, comprised within the phosphorylatable peptide sequence listed in corresponding Column G, Rows 61-64, of Table 1 (SEQ ID NOs: 60-63), wherein said antibody does not bind said protein when not phosphorylated at said tyrosine.
(ii) An equivalent antibody to (i) above that only binds the Protein Kinase when not phosphorylated at the disclosed site (and does not bind the protein when it is phosphorylated at the site).
(iii) A heavy-isotope labeled peptide (AQUA peptide) for the quantification of a Protein Kinase selected from Column A, Rows 61-64, said labeled peptide comprising the phosphorylatable peptide sequence listed in corresponding Column G, Rows 61-64 of Table 1 (SEQ ID NOs: 60-63), which sequence comprises the phosphorylatable tyrosine listed in corresponding Column F, Rows 61-64, of Table 1.

Among this preferred subset of reagents, antibodies and AQUA peptides for the detection/quantification of the following Protein Kinase phosphorylation sites are particularly preferred: Cdk6 (Y13, Y24), and ZAP70 (Y248) (see SEQ ID NOs: 60, 61, and 63).

In a second subset of preferred embodiments there is provided:
(i) An antibody that specifically binds an Adaptor/Scaffold protein protein selected from Column A, Rows 8-14, of Table 1 only when phosphorylated at the tyrosine listed in corresponding Column F, Rows 8-14, of Table 1, comprised within the phosphorylatable peptide sequence listed in corresponding Column G, Rows 8-14, of Table 1 (SEQ ID NOs: 7-13), wherein said antibody does not bind said protein when not phosphorylated at said tyrosine.

(ii) An equivalent antibody to (i) above that only binds the Adaptor/Scaffold protein when not phosphorylated at the disclosed site (and does not bind the protein when it is phosphorylated at the site).

(iii) A heavy-isotope labeled peptide (AQUA peptide) for the quantification of an Adaptor/Scaffold protein selected from Column A, Rows 8-14, said labeled peptide comprising the phosphorylatable peptide sequence listed in corresponding Column G, Rows 8-14, of Table 1 (SEQ ID NOs: 7-13), which sequence comprises the phosphorylatable tyrosine listed in corresponding Column F, Rows 8-14, of Table 1.

Among this preferred subset of reagents, antibodies and AQUA peptides for the detection/quantification of the following Adaptor/Scaffold protein phosphorylation sites are particularly preferred: CASKIN2 (Y384), SIT (Y95), and LPP (Y317) (see SEQ ID NOs: 7, 12, and 13).

In another subset of preferred embodiments there is provided:
(i) An isolated phosphorylation site-specific antibody that specifically binds a Transcription Factor/Initiation Complex protein selected from Column A, Rows 78-86, of Table 1 only when phosphorylated at the tyrosine listed in corresponding Column F, Rows 78-86, of Table 1, comprised within the phosphorylatable peptide sequence listed in corresponding Column G, Rows 78-86, of Table 1 (SEQ ID NOs: 77-85), wherein said antibody does not bind said protein when not phosphorylated at said tyrosine.
(ii) An equivalent antibody to (i) above that only binds the Transcription Factor/initiation Complex protein when not phosphorylated at the disclosed site (and does not bind the protein when it is phosphorylated at the site).
(iii) A heavy-isotope labeled peptide (AQUA peptide) for the quantification of a Transcription Factor/initiation Complex protein selected from Column A, Rows 78-86, said labeled peptide comprising the phosphorylatable peptide sequence listed in corresponding Column G, Rows 78-86, of Table 1 (SEQ ID NOs: 77-85), which sequence comprises the phosphorylatable tyrosine listed in corresponding Column F, Rows 78-86, of Table 1.

Among this preferred subset of reagents, antibodies and AQUA peptides for the detection/quantification of the following Transcription Factor/Initiation Complex protein phosphorylation sites are particularly preferred: Ets-1 (Y205, Y223), and Max (Y123) (see SEQ ID NOs: 77, 78, and 81).

In still another subset of preferred embodiments there is provided:
(i) An isolated phosphorylation site-specific antibody that specifically binds a Transcription Coactivator/Corepressor protein selected from Column A, Rows 87-88 of Table 1 only when phosphorylated at the tyrosine listed in corresponding Column F, Rows 87-88, of Table 1, comprised within the phosphorylatable peptide sequence listed in corresponding Column G, Rows 87-88, of Table 1 (SEQ ID NOs: 86-87), wherein said antibody does not bind said protein when not phosphorylated at said tyrosine.
(ii) An equivalent antibody to (i) above that only binds the Transcription Coactivator/Corepressor protein when not phosphorylated at the disclosed site (and does not bind the protein when it is phosphorylated at the site).
(iii) A heavy-isotope labeled peptide (AQUA peptide) for the quantification of a Transcription Coactivator/Corepressor protein selected from Column A, Rows 87-88, said labeled peptide comprising the phosphorylatable peptide sequence listed in corresponding Column G, Rows 87-88, of Table 1 (SEQ ID NOs: 86-87), which sequence comprises the phosphorylatable tyrosine listed in corresponding Column F, Rows 87-88, of Table 1.

In still another subset of preferred embodiments there is provided:
(i) An isolated phosphorylation site-specific antibody that specifically binds an Actin Binding protein selected from Column A, Rows 2-7, of Table 1 only when phosphorylated at the tyrosine listed in corresponding Column F, Rows 2-7, of Table 1, comprised within the phosphorylatable peptide sequence listed in corresponding Column G, Rows 2-7 of Table 1 (SEQ ID NOs: 1-6), wherein said antibody does not bind said protein when not phosphorylated at said tyrosine.
(ii) An equivalent antibody to (i) above that only binds the Actin Binding protein when not phosphorylated at the disclosed site (and does not bind the protein when it is phosphorylated at the site).
(iii) A heavy-isotope labeled peptide (AQUA peptide) for the quantification of an Actin Binding protein selected from Column A, Rows 2-7, said labeled peptide comprising the phosphorylatable peptide sequence listed in corresponding Column G, Rows 2-7, of Table 1 (SEQ ID NOs: 1-6), which sequence comprises the phosphorylatable tyrosine listed in corresponding Column F, Rows 2-7, of Table 1.

Among this preferred subset of reagents, antibodies and AQUA peptides for the detection/quantification of the following Actin Binding protein phosphorylation sites are particularly preferred: Y1047 in Filamin A, (see SEQ ID NO: 6).

In yet another subset of preferred embodiments, there is provided:
(i) An isolated phosphorylation site-specific antibody that specifically binds a Cytoskeletal protein selected from Column A, Rows 33-44, of Table 1 only when phosphorylated at the tyrosine listed in corresponding Column F, Rows 33-44, of Table 1, comprised within the phosphorylatable peptide sequence listed in corresponding Column G, Rows 33-44, of Table 1 (SEQ ID NOs: 32-43), wherein said antibody does not bind said protein when not phosphorylated at said tyrosine.
(ii) An equivalent antibody to (i) above that only binds the Cytoskeletal protein when not phosphorylated at the disclosed site (and does not bind the protein when it is phosphorylated at the site).
(iii) A heavy-isotope labeled peptide (AQUA peptide) for the quantification of an T-cell receptor signaling protein that is a Cytoskeletal protein selected from Column A, Rows 33-44, said labeled peptide comprising the phosphorylatable peptide sequence listed in corresponding Column G, Rows 33-44, of Table 1 (SEQ ID NOs: 32-43), which sequence comprises the phosphorylatable tyrosine listed in corresponding Column F, Rows 33-44, of Table 1.

Among this preferred subset of reagents, antibodies and AQUA peptides for the detection/quantification of the following Cytoskeletal protein phosphorylation sites are particularly preferred: Cortactin (Y453) (see SEQ ID NO: 43).

In yet another subset of preferred embodiments, there is provided:
(i) An isolated phosphorylation site-specific antibody specifically binds an RNA Binding protein selected from Column A, Rows 69-77, of Table 1 only when phosphorylated at the tyrosine listed in corresponding Column F, Rows 69-77, of Table 1, comprised within the phosphorylatable peptide sequence listed in corresponding Column G, Rows 69-77, of Table 1 (SEQ ID NOs: 68-76), wherein said antibody does not bind said protein when not phosphorylated at said tyrosine.

(ii) An equivalent antibody to (i) above that only binds the RNA Binding protein when not phosphorylated at the disclosed site (and does not bind the protein when it is phosphorylated at the site).

(iii) A heavy-isotope labeled peptide (AQUA peptide) for the quantification of an T-cell receptor signaling protein that is an RNA Binding protein selected from Column A, Rows 69-77, said labeled peptide comprising the phosphorylatable peptide sequence listed in corresponding Column G, Rows 69-77, of Table 1 (SEQ ID NOs: 68-76), which sequence comprises the phosphorylatable tyrosine listed in corresponding Column F, Rows 69-77, of Table 1.

Among this preferred subset of reagents, antibodies and AQUA peptides for the detection/quantification of the following RNA Binding protein phosphorylation sites are particularly preferred: snRNP C (Y8 and Y12) (see SEQ ID NOs: 75 and 76).

In yet another subset of preferred embodiments, there is provided:

(i) An isolated phosphorylation site-specific antibody that specifically binds a Translation Initiation Complex protein selected from Column A, Rows 89-91, of Table 1 only when phosphorylated at the tyrosine listed in corresponding Column F, Rows 89-91, of Table 1, comprised within the phosphorylatable peptide sequence listed in corresponding Column G, Rows 89-91, of Table 1 (SEQ ID NOs: 88-90), wherein said antibody does not bind said protein when not phosphorylated at said tyrosine.

(ii) An equivalent antibody to (i) above that only binds the Translation Initiation Complex protein when not phosphorylated at the disclosed site (and does not bind the protein when it is phosphorylated at the site).

(iii) A heavy-isotope labeled peptide (AQUA peptide) for the quantification of an T-cell receptor signaling protein that is a Translation Initiation Complex protein selected from Column A, Rows 89-91, said labeled peptide comprising the phosphorylatable peptide sequence listed in corresponding Column G, Rows 89-91, of Table 1 (SEQ ID NOs: 88-90), which sequence comprises the phosphorylatable tyrosine listed in corresponding Column F, Rows 89-91, of Table 1.

Among this preferred subset of reagents, antibodies and AQUA peptides for the detection/quantification of the following Translation Initiation Complex protein phosphorylation sites are particularly preferred: eIF4G (Y594), and eIF4H (Y101) (see SEQ ID NOs: 88 and 89).

In still another subset of preferred embodiments, there is provided:

(i) An isolated phosphorylation site-specific antibody that specifically binds a G Protein Regulator/GTPase Activating protein selected from Column A, Rows 47-51, of Table 1 only when phosphorylated at the tyrosine listed in corresponding Column F, Rows 47-51, of Table 1, comprised within the phosphorylatable peptide sequence listed in corresponding Column G, Rows 47-51, of Table 1 (SEQ ID NOs: 46-50), wherein said antibody does not bind said protein when not phosphorylated at said tyrosine.

(ii) An equivalent antibody to (i) above that only binds the G Protein Regulator/GTPase Activating protein when not phosphorylated at the disclosed site (and does not bind the protein when it is phosphorylated at the site).

(iii) A heavy-isotope labeled peptide (AQUA peptide) for the quantification of an T-cell receptor signaling protein that is a G Protein Regulator/GTPase Activating protein selected from Column A, Rows 47-51, said labeled peptide comprising the phosphorylatable peptide sequence listed in corresponding Column G, Rows 47-51, of Table 1 (SEQ ID NOs: 46-50), which sequence comprises the phosphorylatable tyrosine listed in corresponding Column F, Rows 47-51, of Table 1.

Among this preferred subset of reagents, antibodies and AQUA peptides for the detection/quantification of the following G Protein Regulator/GTPase Activating protein phosphorylation sites are particularly preferred: GIT2 (Y484, Y492) (see SEQ ID NOs: 49 and 50).

In still another subset of preferred embodiments, there is provided:

(i) An isolated phosphorylation site-specific antibody that specifically binds a Receptor protein selected from Column A, Rows 66-68, of Table 1 only when phosphorylated at the tyrosine listed in corresponding Column F, Rows 66-68, of Table 1, comprised within the phosphorylatable peptide sequence listed in corresponding Column G, Rows 66-68, of Table 1 (SEQ ID NOs: 65-67), wherein said antibody does not bind said protein when not phosphorylated at said tyrosine.

(ii) An equivalent antibody to (i) above that only binds the Receptor protein when not phosphorylated at the disclosed site (and does not bind the protein when it is phosphorylated at the site).

(iii) A heavy-isotope labeled peptide (AQUA peptide) for the quantification of an T-cell receptor signaling protein that is a Receptor protein selected from Column A, Rows 66-68, said labeled peptide comprising the phosphorylatable peptide sequence listed in corresponding Column G, Rows 66-68, of Table 1 (SEQ ID NOs: 65-67), which sequence comprises the phosphorylatable tyrosine listed in corresponding Column F, Rows 66-68, of Table 1.

In yet a further subset of preferred embodiments, there is provided:

(i) An isolated phosphorylation site-specific antibody that specifically binds a protein selected from the group consisting of Bid, RCAS1, Cdc37, PIP5K, HYD, FAF-X, and UBE1 (Column A, Rows 18, 19, 25, 53, 54, 60, and 92 of Table 1) only when phosphorylated at the tyrosine listed in corresponding Column F, Rows 18, 19, 25, 53, 54, 60, and 92 of Table 1), said tyrosine comprised within the phosphorylatable peptide sequence listed in corresponding Column G, Rows 18, 19, 25, 53, 54, 60, and 92, of Table 1 (SEQ ID NOs: 17, 18, 24, 52, 53, 59, and 91), wherein said antibody does not bind said protein when not phosphorylated at said tyrosine.

(ii) An equivalent antibody to (i) above that only binds the Bid, RCAS1, Cdc37, PIP5K, HYD, FAF-X, and UBE1 protein when not phosphorylated at the disclosed site (and does not bind the protein when it is phosphorylated at the site).

(iii) A heavy-isotope labeled peptide (AQUA peptide) for the quantification of a protein selected from the group consisting of Bid, RCAS1, Cdc37, PIP5K, HYD, FAF-X, and UBE1 (Column A, Rows 18, 19, 25, 53, 54, 60, and 92 of Table 1), said labeled peptide comprising the phosphorylatable peptide sequence listed in corresponding Column G, Rows 18, 19, 25, 53, 54, 60, and 92, of Table 1 (SEQ ID NOs: 17, 18, 24, 52, 53, 59, and 91), which sequence comprises the phosphorylatable tyrosine listed in corresponding Column F, Rows 18, 19, 25, 53, 54, 60, and 92, of Table 1.

The invention also provides, in part, an immortalized cell line producing an antibody of the invention, for example, a cell line producing an antibody within any of the foregoing preferred subsets of antibodies. In one preferred embodiment, the immortalized cell line is a rabbit hybridoma or a mouse hybridoma.

In certain other preferred embodiments, a heavy-isotope labeled peptide (AQUA peptide) of the invention (for example, an AQUA peptide within an of the foregoing preferred subsets of AQUA peptides) comprises a disclosed site sequence wherein the phosphorylatable tyrosine is phosphorylated. In certain other preferred embodiments, a heavy-isotope labeled peptide of the invention comprises a disclosed site sequence wherein the phosphorylatable tyrosine is not phosphorylated.

The foregoing subsets of preferred reagents of the invention should not be construed as limiting the scope of the invention, which, as noted above, includes reagents for the detection and/or quantification of disclosed phosphorylation sites on any of the other protein type/group subsets (each a preferred subset) listed in Column D of Table 1/FIG. 2.

Also provided by the invention are methods for detecting or quantifying a T-cell receptor signaling protein that is tyrosine-phosphorylated, said method comprising the step of utilizing one or more of the above-described reagents of the invention to detect or quantify one or more T-cell receptor signaling protein(s) selected from Column A of Table 1 only when phosphorylated at the tyrosine listed in corresponding Column F of Table 1. In certain preferred embodiments of the methods of the invention, the reagents comprise a subset of preferred reagents as described above.

The identification of the disclosed novel T-cell receptor signaling protein phosphorylation sites, and the standard production and use of the reagents provided by the invention are described in further detail below and in the Examples that follow.

All cited references are hereby incorporated herein, in their entirety, by reference. The Examples are provided to further illustrate the invention, and do not in any way limit its scope, except as provided in the claims appended hereto.

TABLE 1

Newly-Discovered T-cell Receptor Signaling Protein Phosphorylation Sites.

| | A | C | D | F | G | H |
|---|---|---|---|---|---|---|
| 1 | Protein Name (short) | Accession Number | Protein Type | Phospho-Residue | Phosphorylation Site Sequence | SEQ ID NO: |
| 2 | abLIM | O14639 | Actin binding protein | 396 | IPKVKAIyDIERPDL | SEQ ID NO: 1 |
| 3 | abLIM | O14639 | Actin binding protein | 406 | ERPDLITyEPFYTSG | SEQ ID NO: 2 |
| 4 | abLIM | O14639 | Actin binding protein | 410 | LITYEPFyTSGYDDK | SEQ ID NO: 3 |
| 5 | Drebrin 1 | Q16643 | Actin binding protein | 622 | KAPPPVFyNKPPEID | SEQ ID NO: 4 |
| 6 | Drebrin F | Q9UJU6 | Actin binding protein | 162 | QAPVGSVyQKTNAVS | SEQ ID NO: 5 |
| 7 | Filamin A | P21333 | Actin binding protein | 1047 | PYEVEVTyDGVPVPG | SEQ ID NO: 6 |
| 8 | CASKIN2 | Q8WXE0 | Adaptor/scaffold | 384 | EPPHPLTySQLPRVG | SEQ ID NO: 7 |
| 9 | DOCK2 | Q92608 | Adaptor/scaffold | 221 | MSKDQPDyAMYSRIS | SEQ ID NO: 8 |
| 10 | DOCK2 | Q92608 | Adaptor/scaffold | 224 | DQPDYAMySRISSSP | SEQ ID NO: 9 |
| 11 | LIM | O60705 | Adaptor/scaffold | 251 | VERYTEFyHVPTHSD | SEQ ID NO: 10 |
| 12 | NRAGE | Q9Y5V3 | Adaptor/scaffold | 92 | TKGPNGVyDFSQAHN | SEQ ID NO: 11 |
| 13 | SIT | Q9Y3P8 | Adaptor/scaffold | 95 | PLYGNLHyLQTGRLS | SEQ ID NO: 12 |
| 14 | LPP | Q93052 | Adaptor/scaffold, Cytoskeletal protein | 317 | RNDSDPTyGQQGHPN | SEQ ID NO: 13 |
| 15 | Erbin | Q96RT1 | Adhesion | 972 | PQSAPQIyGPPQYNI | SEQ ID NO: 14 |
| 16 | Erbin | Q96RT1 | Adhesion | 981 | PPQYNIQySSSAAVK | SEQ ID NO: 15 |
| 17 | Erbin | Q96RT1 | Adhesion | 1107 | PEGDYLSyREFHSAG | SEQ ID NO: 16 |

TABLE 1-continued

Newly-Discovered T-cell Receptor Signaling Protein Phosphorylation Sites.

| | A<br>Protein<br>Name<br>(short) | C<br>Accession<br>Number | D<br>Protein<br>Type | F<br>Phospho-<br>Residue | G<br>Phosphory-<br>lation<br>Site Sequence | H<br>SEQ<br>ID<br>NO: |
|---|---|---|---|---|---|---|
| 18 | Bid | P55957 | Apoptosis | 54 | LAPQWEGyDELQTDG | SEQ ID NO: 17 |
| 19 | RCAS1 | O00559 | Apoptosis | 94 | LEQLEPDyFKDMTPT | SEQ ID NO: 18 |
| 20 | BAG3 | O95817 | Apoptosis, Chaperone | 247 | YQTHQPVyHKIQGDD | SEQ ID NO: 19 |
| 21 | EHD4 | Q9H223 | Calcium-binding protein | 451 | VAKDKPVyDELFYTL | SEQ ID NO: 20 |
| 22 | EHD4 | Q9H223 | Calcium-binding protein | 456 | PVYDELFyTLSPING | SEQ ID NO: 21 |
| 23 | SGT1 | Q9Y2Z0 | Cell cycle regulation | 285 | NRLFQQIySDGSDEV | SEQ ID NO: 22 |
| 24 | Kv-beta2 | Q13303 | Channel, potassium | 25 | TGSPGMIySTRYGSP | SEQ ID NO: 23 |
| 25 | Cdc37 | Q16543 | Chaperone | 298 | GLDPVEVyESLPEEL | SEQ ID NO: 24 |
| 26 | FKBP8 | Q14318 | Chaperone | 265 | VLAQQGEySEAIPIL | SEQ ID NO: 25 |
| 27 | HDJ2 | P31689 | Chaperone | 381 | RHYNGEAyEDDEHHP | SEQ ID NO: 26 |
| 28 | STI1 | P31948 | Chaperone | 354 | KEQERLAyINPDLAL | SEQ ID NO: 27 |
| 29 | TBCB | Q99426 | Chaperone, Cytoskeletal protein | 98 | SGARLGEyEDVSRVE | SEQ ID NO: 28 |
| 30 | TBCB | Q99426 | Chaperone, Cytoskeletal protein | 114 | YTISQEAyDQRQDTV | SEQ ID NO: 29 |
| 31 | CD46 | P15529 | Cofactor | 384 | KADGGAEyATYQTKS | SEQ ID NO: 30 |
| 32 | CD46 | P15529 | Cofactor | 387 | GGAEYATyQTKSTTP | SEQ ID NO: 31 |
| 33 | CLIM1 | O00151 | Cytoskeletal protein | 144 | ARVITNQyNNPAGLY | SEQ ID NO: 32 |
| 34 | CLIM1 | O00151 | Cytoskeletal protein | 151 | YNNPAGLySSENISN | SEQ ID NO: 33 |
| 35 | EB1 | Q15691 | Cytoskeletal protein | 124 | ANYDGKDyDPVAARQ | SEQ ID NO: 34 |
| 36 | Emerin | P50402 | Cytoskeletal protein | 85 | KKEDALLyQSKGYND | SEQ ID NO: 35 |
| 37 | Emerin | P50402 | Cytoskeletal protein | 95 | KGYNDDYyEESYFTT | SEQ ID NO: 36 |
| 38 | Emerin | P50402 | Cytoskeletal protein | 99 | DDYYEESyFTTRTYG | SEQ ID NO: 37 |
| 39 | MAP1A | P78559 | Cytoskeletal protein | 773 | PRFHTSTyDLPGPEG | SEQ ID NO: 38 |
| 40 | NUDE1 | Q9NXR1 | Cytoskeletal protein | 279 | ASCRNLVyDQSPNRT | SEQ ID NO: 39 |
| 41 | RP1 | Q15555 | Cytoskeletal protein | 167 | ANYDGKEyDPVEARQ | SEQ ID NO: 40 |

TABLE 1-continued

Newly-Discovered T-cell Receptor Signaling Protein Phosphorylation Sites.

| A<br>Protein Name<br>(short) | C<br>Accession Number | D<br>Protein Type | F<br>Phospho-Residue | G<br>Phosphorylation Site Sequence | H<br>SEQ ID NO: |
|---|---|---|---|---|---|
| 42 tubulin, alpha-1 | P05209 | Cytoskeletal protein | 357 | GFKVGINyQPPTVVP | SEQ ID NO: 41 |
| 43 tubulin, beta-1 | P07437 | Cytoskeletal protein | 36 | GIDPTGTyHGDSDLQ | SEQ ID NO: 42 |
| 44 cortactin | Q14247 | Cytoskeletal protein, Actin binding protein | 453 | YSMEAADyREASSQQ | SEQ ID NO: 43 |
| 45 ZNF330 | Q9Y3S2 | DNA binding protein | 308 | NLNLGRTyASGYAHY | SEQ ID NO: 44 |
| 46 ZNF330 | Q9Y3S2 | DNA binding protein | 315 | YASGYAHyEEQEN | SEQ ID NO: 45 |
| 47 Rho-GDI beta | P52566 | G protein regulator, misc. | 24 | ELDSKLNyKPPPQKS | SEQ ID NO: 46 |
| 48 ARF GAP 3 | Q9NP61 | GTPase activating protein, ARF | 349 | NDDSDDSyFTSSSSY | SEQ ID NO: 47 |
| 49 centaurin-beta 2 | Q15057 | GTPase activating protein, ARF | 750 | GQPGDETyQDIFRDF | SEQ ID NO: 48 |
| 50 GIT2 | Q14161 | GTPase activating protein, ARF | 484 | KQATTNVyQVQTGSE | SEQ ID NO: 49 |
| 51 GIT2 | Q14161 | GTPase activating protein, ARF | 492 | QVQTGSEyTDTSNHS | SEQ ID NO: 50 |
| 52 PPP1R11 | O60927 | Inhibitor protein | 64 | SSKCCCIyEKPRAFG | SEQ ID NO: 51 |
| 53 PIP5K | Q9Y2I7 | Kinase, lipid | 1772 | LRGADSAyYQVGQTG | SEQ ID NO: 52 |
| 54 HYD | O95071 | Ligase, Ubiquitin conjugating system | 1746 | ASSAGLIyIDPSNLR | SEQ ID NO: 53 |
| 55 endofin | Q7Z3T8 | Lipid binding protein | 219 | DTTLSDSyNYSGTEN | SEQ ID NO: 54 |
| 56 endofin | Q7Z3T8 | Lipid binding protein | 221 | TLSDSYNySGTENLK | SEQ ID NO: 55 |
| 57 NuMA-1 | Q14980 | Nuclear, misc. | 1774 | VESLESLyFTPIPAR | SEQ ID NO: 56 |
| 58 1-Cys PRX | P30041 | Oxidoreductase | 88 | WSKDINAyNCEEPTE | SEQ ID NO: 57 |
| 59 NKEF-A | Q06830 | Oxidoreductase | 194 | DVQKSKEyFSKQK | SEQ ID NO: 58 |
| 60 FAF-X | Q93008 | Protease (non-proteasomal) | 2533 | GQRAQENyEGSEEVS | SEQ ID NO: 59 |
| 61 Cdk6 | Q00534 | Protein kinase, Ser/Thr (non-receptor), CMGC group, CDK family, CDK4 subfamily | 13 | LCRADQQyECVAEIG | SEQ ID NO: 60 |

TABLE 1-continued

Newly-Discovered T-cell Receptor Signaling Protein Phosphorylation Sites.

| | A | C | D | F | G | H |
|---|---|---|---|---|---|---|
| 1 | Protein Name (short) | Accession Number | Protein Type | Phospho-Residue | Phosphorylation Site Sequence | SEQ ID NO: |
| 62 | Cdk6 | Q00534 | Protein kinase, Ser/Thr (non-receptor), CMGC group, CDK family, CDK4 subfamily | 24 | AEIGEGAyGKVFKAR | SEQ ID NO: 61 |
| 63 | SRPK2 | P78362 | Protein kinase, Ser/Thr (non-receptor), CMGC group, SRPK family, N/A subfamily | 318 | SNDQDGEyCPEVKLK | SEQ ID NO: 62 |
| 64 | ZAP70 | P43403 | Protein kinase, tyrosine (non-receptor), TK group, Syk family, N/A subfamily | 248 | LKADGLIyCLKEACP | SEQ ID NO: 63 |
| 65 | PTP1B | P18031 | Protein phosphatase, tyrosine (non-receptor) | 20 | SGSWAAIyQDIRHEA | SEQ ID NO: 64 |
| 66 | SRPR | P08240 | Receptor, misc. | 261 | ANKEVLDySTPTTNG | SEQ ID NO: 65 |
| 67 | LDLR | P01130 | Receptor, protein translocating | 845 | ICHNQDGySYPSRQM | SEQ ID NO: 66 |
| 68 | TfR | P02786 | Receptor, protein translocating | 20 | FGGEPLSyTRFSLAR | SEQ ID NO: 67 |
| 69 | hnRNP 2H9 | P31942 | RNA binding protein | 296 | GMDNQGGyGSVGRMG | SEQ ID NO: 68 |
| 70 | hnRNP A0 | Q13151 | RNA binding protein | 180 | AVPKEDIySGGGGGGG | SEQ ID NO: 69 |
| 71 | hnRNP F | P52597 | RNA binding protein | 246 | GYGGYEEySGLSDGY | SEQ ID NO: 70 |
| 72 | hnRNP H' | P55795 | RNA binding protein | 246 | GYGGYDDyNGYNDGY | SEQ ID NO: 71 |
| 73 | RBM4 | Q9BWF3 | RNA binding protein | 190 | VADLTEQyNEQYGAV | SEQ ID NO: 72 |
| 74 | RBM4 | Q9BWF3 | RNA binding protein | 194 | TEQYNEQyGAVRTPY | SEQ ID NO: 73 |
| 75 | SF3A1 | Q15459 | RNA binding protein | 456 | KQSDDEVyAPGLDIE | SEQ ID NO: 74 |
| 76 | snRNP C | P09234 | RNA binding protein | 8 | MPKFYCDyCDTYLTH | SEQ ID NO: 75 |
| 77 | snRNP C | P09234 | RNA binding protein | 12 | YCDYCDTyLTHDSPS | SEQ ID NO: 76 |
| 78 | Ets-1 | P14921 | Transcription factor | 205 | SLKYENDyPSVILRD | SEQ ID NO: 77 |
| 79 | Ets-1 | P14921 | Transcription factor | 223 | TDTLQNDyFAIKQEV | SEQ ID NO: 78 |

TABLE 1-continued

Newly-Discovered T-cell Receptor Signaling Protein Phosphorylation Sites.

| | Protein Name (short) | Accession Number | Protein Type | Phospho-Residue | Phosphorylation Site Sequence | SEQ ID NO: |
|---|---|---|---|---|---|---|
| 80 | FUBP1 | Q96AE4 | Transcription factor | 58 | TSLNSNDyGYGGQKR | SEQ ID NO: 79 |
| 81 | Kaiso | O00319 | Transcription factor | 443 | ANIGEDTyDIVIPVK | SEQ ID NO: 80 |
| 82 | Max | P25912 | Transcription factor | 123 | PSSDNSLyTNAKGST | SEQ ID NO: 81 |
| 83 | NSBP1 | P82970 | Transcription factor | 76 | EAVVEEDyNENAKNG | SEQ ID NO: 82 |
| 84 | YB-1 | P16991 | Transcription factor | 162 | PRNYQQNyQNSESGE | SEQ ID NO: 83 |
| 85 | ZFP 598 | Q86UK7 | Transcription factor | 306 | GVVGGEDyEEVDRYS | SEQ ID NO: 84 |
| 86 | RPA40 | O15160 | Transcription, initiation complex | 33 | TTDFPGNySGYDDAW | SEQ ID NO: 85 |
| 87 | AIP | O00170 | Transcription, coactivator/ corepressor | 248 | KLVVEEYyEVLDHCS | SEQ ID NO: 86 |
| 88 | TRIP4 | Q15650 | Transcription, coactivator/ corepressor | 289 | VIDDESDyFASDSNQ | SEQ ID NO: 87 |
| 89 | eIF4G | Q04637 | Translation initiation complex | 594 | IQPGEQKyEYKSDQW | SEQ ID NO: 88 |
| 90 | eIF4H | Q15056 | Translation initiation complex | 101 | SLKEALTyDGALLGD | SEQ ID NO: 89 |
| 91 | RPS3a | P49241 | Translation initiation complex | 255 | KVERADGyEPPVQES | SEQ ID NO: 90 |
| 92 | UBE1 | P22314 | Ubiquitin conjugating system | 55 | ADIDEGLySRQLYVL | SEQ ID NO: 91 |
| 93 | TACC1 | O75410 | Unknown (putative breast cancer candidate gene) | 533 | EPEEDLEyFECSNVP | SEQ ID NO: 92 |
| 94 | SCAMP3 | NP_005689 | Vesicle protein | 53 | TREPPPAyEPPAPAP | SEQ ID NO: 93 |
| 95 | SNAP-gamma | Q99747 | Vesicle protein | 307 | ADEEEDEySGGLC | SEQ ID NO: 94 |
| 96 | SNX12 | Q9UMY4 | Vesicle protein | 23 | PQDLTDAyGPPSNFL | SEQ ID NO: 95 |

The short name for each protein in which a phosphorylation site has presently been identified is provided in Column A, and it accession number (human) is provided Column C. The protein type/group into which each protein falls is provided in Column D. The identified tyrosine residue at which phosphorylation occurs in a given protein is identified in Column F, and the amino acid sequence of the phosphorylation site encompassing the tyrosine residue is provided in Column G (lower case y=the tyrosine (identified in Column F) at which phosphorylation occurs. Table 1 above is identical to FIG. 2, except that the latter includes the full protein name (Column B).

The identification of these 95 phosphorylation sites is described in more detail in Part A below and in Example 1.

Definitions

As used herein, the following terms have the meanings indicated:

"Antibody" or "antibodies" refers to all types of immunoglobulins, including IgG, IgM, IgA, IgD, and IgE, including $F_{ab}$ or antigen-recognition fragments thereof, including chimeric, polyclonal, and monoclonal antibodies. The term "does not bind" with respect to an antibody's binding to one phospho-form of a sequence means does not substantially react with as compared to the antibody's binding to the other phospho-form of the sequence for which the antibody is specific.

"T-cell receptor signaling protein" means any protein (or polypeptide derived therefrom) enumerated in Column A of Table 1/FIG. 2, which is disclosed herein as being phosphorylated in one or more cell line(s) in which T-cell receptor signaling is activated. T-cell receptor signaling proteins may be direct substrates of T-cell receptor itself, or may be indirect substrates downstream in T-cell receptor signaling pathways. A T-cell receptor signaling protein may also be phosphorylated in other cell lines harboring activated kinase activity.

"Heavy-isotope labeled peptide" (used interchangeably with AQUA peptide) means a peptide comprising at least one heavy-isotope label, which is suitable for absolute quantification or detection of a protein as described in WO/03016861, "Absolute Quantification of Proteins and Modified Forms Thereof by Multistage Mass Spectrometry" (Gygi et al.), further discussed below.

"Protein" is used interchangeably with polypeptide, and includes protein fragments and domains as well as whole protein.

"Phosphorylatable amino acid" means any amino acid that is capable of being modified by addition of a phosphate group, and includes both forms of such amino acid.

"Phosphorylatable peptide sequence" means a peptide sequence comprising a phosphorylatable amino acid.

"Phosphorylation site-specific antibody" means an antibody that specifically binds a phosphorylatable peptide sequence/epitope only when phosphorylated, or only when not phosphorylated, respectively. The term is used interchangeably with "phospho-specific" antibody.

A. Identification of Novel T-cell Receptor Signaling Protein Phosphorylation Sites.

The 95 novel T-cell receptor signaling protein phosphorylation sites disclosed herein and listed in Table 1/FIG. 2 were discovered by employing the modified peptide isolation and characterization techniques described in described in "Immunoaffinity Isolation of Modified Peptides From Complex Mixtures," U.S. Patent Publication No. 20030044848, Rush et al. (the teaching of which is hereby incorporated herein by reference, in its entirety) using cellular extracts from a Jurkat cell line in which the T-cell receptor signaling is constitutively activated. The isolation and identification of phosphopeptides from this T-cell line, using an immobilized general phosphotyrosine-specific antibody, is described in detail in Example 1 below. In addition to the 95 previously unknown protein phosphorylation sites discovered, many known phosphorylation sites were also identified (not described herein). The immunoaffinity/mass spectrometric technique described in the '848 Patent Publication (the "IAP" method)—and employed as described in detail in the Examples—is briefly summarized below.

The IAP method employed generally comprises the following steps: (a) a proteinaceous preparation (e.g. a digested cell extract) comprising phosphopeptides from two or more different proteins is obtained from an organism; (b) the preparation is contacted with at least one immobilized general phosphotyrosine-specific antibody; (c) at least one phosphopeptide specifically bound by the immobilized antibody in step (b) is isolated; and (d) the modified peptide isolated in step (c) is characterized by mass spectrometry (MS) and/or tandem mass spectrometry (MS-MS). Subsequently, (e) a search program (e.g. Sequest) may be utilized to substantially match the spectra obtained for the isolated, modified peptide during the characterization of step (d) with the spectra for a known peptide sequence. A quantification step employing, e.g. SILAC or AQUA, may also be employed to quantify isolated peptides in order to compare peptide levels in a sample to a baseline.

In the IAP method as employed herein, a general phosphotyrosine-specific monoclonal antibody (commercially available from Cell Signaling Technology, Inc., Beverly, Mass., Cat #9411 (p-Tyr-100)) was used in the immunoaffinity step to isolate the widest possible number of phospho-tyrosine containing peptides from the T-cell extracts.

Extracts from a pervanadate-treated Jurkat cell line were employed. This established cell line is derived from patients with acute lymphoblastic leukemia and leukemic transformed non-Hodgkin lymphoma, in which T-cell receptor signaling pathways are constitutively activated.

As described in more detail in the Examples, lysates were prepared from this cell line and digested with trypsin after treatment with DTT and iodoacetamide to alkylate cysteine residues. Before the immunoaffinity step, peptides were pre-fractionated by reversed-phase solid phase extraction using Sep-Pak $C_{18}$ columns to separate peptides from other cellular components. The solid phase extraction cartridges were eluted with varying steps of acetonitrile. Each lyophilized peptide fraction was redissolved in PBS and treated with phosphotyrosine antibody (P-Tyr-100, CST #9411) immobilized on protein G-Sepharose. Immunoaffinity-purified peptides were eluted with 0.1% TFA and a portion of this fraction was concentrated with Stage tips and analyzed by LC-MS/MS, using a ThermoFinnigan LCQ Deca XP Plus ion trap mass spectrometer. Peptides were eluted from a 10 cm×75 µm reversed-phase column with a 45-min linear gradient of acetonitrile. MS/MS spectra were evaluated using the program Sequest with the NCBI human protein database.

This revealed a total of 95 novel tyrosine phosphorylation sites in signaling pathways affected by T-cell receptor activation. The identified phosphorylation sites and their parent proteins are enumerated in Table 1/FIG. 2. The tyrosine (human sequence) at which phosphorylation occurs is provided in Column F, and the peptide sequence encompassing the phosphorylatable tyrosine residue at the site is provided in Column G.

As a result of the discovery of these phosphorylation sites, phospho-specific antibodies and AQUA peptides for the detection of and quantification of these sites and their parent proteins may now be produced by standard methods, described below. These new reagents will prove highly useful in studying the signaling pathways and events underlying the progression of diseases mediated by altered T-cell receptor signaling and the identification of new biomarkers and targets for diagnosis and treatment of such diseases.

B. Antibodies and Cell Lines

Isolated phosphorylation site-specific antibodies that specifically bind a T-cell receptor signaling protein disclosed in Column A of Table 1 only when phosphorylated (or only when not phosphorylated) at the corresponding amino acid (tyrosine) and phosphorylation site listed in Columns F and G of Table 1 may now be produced by standard antibody production methods, such as anti-peptide antibody methods, using the phosphorylation site sequence information provided in Column G of Table 1. For example, two previously unknown Cdk6 kinase phosphorylation sites (tyrosines 13 and 24) (see Rows 61-62 of Table 1) are presently disclosed. Thus, antibodies that specifically bind any one of these novel Cdk6 sites can now be produced by using (all or part of) the amino acid sequence encompassing the respective phosphorylated residue as a peptide antigen used to immunize an animal (e.g. a peptide antigen comprising the sequence set forth in Row 61, Column G, of Table 1 (which encompasses the phosphorylated tyrosine at position 13 in Cdk6) may be employed to produce an antibody that only binds Cdk6 when phosphorylated at Tyr13).

Polyclonal antibodies of the invention may be produced according to standard techniques by immunizing a suitable animal (e.g., rabbit, goat, etc.) with a peptide antigen corresponding to the T-cell receptor protein phosphorylation site of interest (i.e. a phosphorylation site enumerated in Column G of Table 1, which comprises the corresponding phosphorylatable amino acid listed in Column F of Table 1), collecting immune serum from the animal, and separating the polyclonal antibodies from the immune serum, in accordance with known procedures. For example, a peptide antigen comprising the novel ZAP70 kinase phosphorylation site disclosed herein (SEQ ID NO: 63=ADGLIpYCLK, encompassing phosphorylated tyrosine 248 (see Row 64 of Table 1)) may be used to produce antibodies that only bind ZAP70 when phosphorylated at Tyr248. Similarly, a peptide comprising any of the phosphorylation site sequences provided in Column G of Table 1 may employed as an antigen to produce an antibody that only binds the corresponding protein listed in Column A of Table 1 when phosphorylated (or when not phosphorylated) at the corresponding residue listed in Column F. If an antibody that only binds the protein when phosphorylated at the disclosed site is desired, the peptide antigen includes the phosphorylated form of the amino acid. Conversely, if an antibody that only binds the protein when not phosphorylated at the disclosed site is desired, the peptide antigen includes the non-phosphorylated form of the amino acid.

Peptide antigens suitable for producing antibodies of the invention may be designed, constructed and employed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, *Methods In Enzymology*, 201: 264-283 (1991); Merrifield, *J. Am. Chem. Soc.* 85:21-49 (1962)).

It will be appreciated by those of skill in the art that longer or shorter phosphopeptide antigens may be employed. See Id. For example, a peptide antigen may consist of the full sequence disclosed in Column G of Table 1, or it may comprise additional amino acids flanking such disclosed sequence, or may comprise of only a portion of the disclosed sequence immediately flanking the phosphorylatable amino acid (indicated in Column G by lowercase "y"). Polyclonal antibodies produced as described herein may be screened as further described below.

Monoclonal antibodies of the invention may be produced in a hybridoma cell line according to the well-known technique of Kohler and Milstein. *Nature* 265: 495-97 (1975); Kohler and Milstein, *Eur. J. Immunol.* 6: 511 (1976); see also, CURRENT PROTOCOLS IN MOLECULAR BIOLOGY, Ausubel et al. Eds. (1989). Monoclonal antibodies so produced are highly specific, and improve the selectivity and specificity of diagnostic assay methods provided by the invention. For example, a solution containing the appropriate antigen may be injected into a mouse or other species and, after a sufficient time (in keeping with conventional techniques), the animal is sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S Pat. No. 5,675,063, C. Knight, Issued Oct. 7, 1997. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, *Science* 246: 1275-81 (1989); Mullinax et al., *Proc. Nat'l Acad. Sci.* 87: 8095 (1990). If monoclonal antibodies of one isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l . Acad. Sci.,* 82: 8653 (1985); Spira et al., *J. Immunol. Methods,* 74: 307 (1984)).

The preferred epitope of a phosphorylation-site specific antibody of the invention is a peptide fragment consisting essentially of about 8 to 17 amino acids including the phosphorylatable tyrosine, wherein about 3 to 8 amino acids are positioned on each side of the phosphorylatable tyrosine (for example, the CASKIN2 tyrosine 384 phosphorylation site sequence disclosed in Row 8, Column G of Table 1), and antibodies of the invention thus specifically bind a target T-cell receptor signaling polypeptide comprising such epitopic sequence. Particularly preferred epitopes bound by the antibodies of the invention comprise all or part of a phosphorylatable site sequence listed in Column G of Table 1, including the phosphorylatable amino acid (tyrosine).

Included in the scope of the invention are equivalent non-antibody molecules, such as protein binding domains or nucleic acid aptamers, which bind, in a phospho-specific manner, to essentially the same phosphorylatable epitope to which the phospho-specific antibodies of the invention bind. See, e.g., Neuberger et al., *Nature* 312: 604 (1984). Such equivalent non-antibody reagents may be suitably employed in the methods of the invention further described below.

Antibodies provided by the invention may be any type of immunoglobulins, including IgG, IgM, IgA, IgD, and IgE, including $F_{ab}$ or antigen-recognition fragments thereof. The antibodies may be monoclonal or polyclonal and may be of any species of origin, including, (for example) mouse, rat, rabbit, horse, or human, or may be chimeric antibodies. See, e.g., M. Walker et al., *Molec. Immunol.* 26: 403-11 (1989);

Morrision et al., *Proc. Nat'l. Acad. Sci.* 81: 6851 (1984); Neuberger et al., *Nature* 312: 604 (1984)). The antibodies may be recombinant monoclonal antibodies produced according to the methods disclosed in U.S. Pat. No. 4,474,893 (Reading) or U.S. Pat. No. 4,816,567 (Cabilly et al.) The antibodies may also be chemically constructed by specific antibodies made according to the method disclosed in U.S. Pat. No. 4,676,980 (Segel et al.)

The invention also provides immortalized cell lines that produce an antibody of the invention. For example, hybridoma clones, constructed as described above, that produce monoclonal antibodies to the T-cell receptor signaling protein phosphorylation sties disclosed herein are also provided. Similarly, the invention includes recombinant cells producing an antibody of the invention, which cells may be constructed by well known techniques; for example the antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

Phosphorylation site-specific antibodies of the invention, whether polyclonal or monoclonal, may be screened for epitope and phospho-specificity according to standard techniques. See, e.g. Czernik et al., *Methods in Enzymology*, 201: 264-283 (1991). For example, the antibodies may be screened against the phospho and non-phospho peptide library by ELISA to ensure specificity for both the desired antigen (i.e. that epitope including a phosphorylation site sequence enumerated in Column G of Table 1) and for reactivity only with the phosphorylated (or non-phosphorylated) form of the antigen. Peptide competition assays may be carried out to confirm lack of reactivity with other phospho-epitopes on the given T-cell receptor signaling protein. The antibodies may also be tested by Western blotting against cell preparations containing the signaling protein, e.g. cell lines over-expressing the target protein, to confirm reactivity with the desired phosphorylated epitope/target.

Specificity against the desired phosphorylated epitope may also be examined by constructing mutants lacking phosphorylatable residues at positions outside the desired epitope known to be phosphorylated, or by mutating the desired phospho-epitope and confirming lack of reactivity. Phosphorylation-site specific antibodies of the invention may exhibit some limited cross-reactivity related epitopes in non-target proteins. This is not unexpected as most antibodies exhibit some degree of cross-reactivity, and anti-peptide antibodies will often cross-react with epitopes having high homology to the immunizing peptide. See, e.g., Czernik, supra. Cross-reactivity with non-target proteins is readily characterized by Western blotting alongside markers of known molecular weight. Amino acid sequences of cross-reacting proteins may be examined to identify sites highly homologous to the T-cell receptor signaling protein epitope for which the antibody of the invention is specific. In certain cases, polyclonal antisera may be exhibit some undesirable general cross-reactivity to phosphotyrosine, which may be removed by further purification of antisera, e.g. over a phosphotyramine column. Antibodies of the invention specifically bind their target protein (i.e. a protein listed in Column A of Table 1/FIG. 2) only when phosphorylated (or only when not phosphorylated, as the case may be) at the site disclosed in corresponding Columns F/G, and do not (substantially) bind to the other form (as compared to the form for which the antibody is specific).

Antibodies may be further characterized via immunohistochemical (IHC) staining using normal and diseased tissues to examine T-cell receptor phosphorylation and activation status in diseased tissue. IHC may be carried out according to well-known techniques. See, e.g., ANTIBODIES: A LABORATORY MANUAL, Chapter 10, Harlow & Lane Eds., Cold Spring Harbor Laboratory (1988). Briefly, paraffin-embedded tissue (e.g. tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

Antibodies may be further characterized by flow cytometry carried out according to standard methods. See Chow et al., *Cytometry (Communications in Clinical Cytometry)* 46: 72-78 (2001). Briefly and by way of example, the following protocol for cytometric analysis may be employed: samples may be centrifuged on Ficoll gradients to remove erythrocytes, and cells may then be fixed with 2% paraformaldehyde for 10 minutes at 37° C. followed by permeabilization in 90% methanol for 30 minutes on ice. Cells may then be stained with the primary phosphorylation-site specific antibody of the invention (which detects an T-cell receptor signal transduction protein enumerated in Table 1), washed and labeled with a fluorescent-labeled secondary antibody. Additional fluorochrome-conjugated marker antibodies (e.g. CD45, CD34) may also be added at this time to aid in the subsequent identification of specific hematopoietic cell types. The cells would then be analyzed on a flow cytometer (e.g. a Beckman Coulter FC500) according to the specific protocols of the instrument used.

Antibodies of the invention may also be advantageously conjugated to fluorescent dyes (e.g. Alexa488, PE) for use in multi-parametric analyses along with other signal transduction (phospho-CrkL, phospho-Erk ½) and/or cell marker (CD34) antibodies.

Phosphorylation-site specific antibodies of the invention specifically bind to a human T-cell receptor signal transduction protein or polypeptide only when phosphorylated at a disclosed site, but are not limited only to binding the human species, per se. The invention includes antibodies that also bind conserved and highly-homologous or identical phosphorylation sites in respective T-cell receptor signaling proteins from other species (e.g. mouse, rat, monkey, yeast), in addition to binding the human phosphorylation site. Highly-homologous sites conserved in other species can readily be identified by standard sequence comparisons, such as using BLAST, with the human T-cell receptor signal transduction protein phosphorylation sites disclosed herein.

C. Heavy-Isotope Labeled Peptides (AQUA Peptides).

The novel T-cell receptor signaling protein phosphorylation sites disclosed herein now enable the production of corresponding heavy-isotope labeled peptides for the absolute quantification of such signaling proteins (both phosphorylated and not phosphorylated at a disclosed site) in biological samples. The production and use of AQUA peptides for the absolute quantification of proteins (AQUA) in complex mixtures has been described. See WO/03016861, "Absolute Quantification of Proteins and Modified Forms Thereof by Multistage Mass Spectrometry," Gygi et al. and also Gerber et al. *Proc. Natl. Acad. Sci. U.S.A.* 100: 6940-5 (2003) (the teachings of which are hereby incorporated herein by reference, in their entirety).

The AQUA methodology employs the introduction of a known quantity of at least one heavy-isotope labeled peptide standard (which has a unique signature detectable by LC-SRM chromatography) into a digested biological sample in order to determine, by comparison to the peptide standard, the absolute quantity of a peptide with the same sequence and protein modification in the biological sample. Briefly, the AQUA methodology has two stages: peptide internal standard selection and validation and method development; and implementation using validated peptide internal standards to detect and quantify a target protein in sample. The method is a powerful technique for detecting and quantifying a given peptide/protein within a complex biological mixture, such as a cell lysate, and may be employed, e.g., to quantify change in protein phosphorylation as a result of drug treatment, or to quantify differences in the level of a protein in different biological states.

Generally, to develop a suitable internal standard, a particular peptide (or modified peptide) within a target protein sequence is chosen based on its amino acid sequence and the particular protease to be used to digest. The peptide is then generated by solid-phase peptide synthesis such that one residue is replaced with that same residue containing stable isotopes ($^{13}C$, $^{15}N$). The result is a peptide that is chemically identical to its native counterpart formed by proteolysis, but is easily distinguishable by MS via a 7-Da mass shift. The newly synthesized AQUA internal standard peptide is then evaluated by LC-MS/MS. This process provides qualitative information about peptide retention by reverse-phase chromatography, ionization efficiency, and fragmentation via collision-induced dissociation. Informative and abundant fragment ions for sets of native and internal standard peptides are chosen and then specifically monitored in rapid succession as a function of chromatographic retention to form a selected reaction monitoring (LC-SRM) method based on the unique profile of the peptide standard.

The second stage of the AQUA strategy is its implementation to measure the amount of a protein or modified protein from complex mixtures. Whole cell lysates are typically fractionated by SDS-PAGE gel electrophoresis, and regions of the gel consistent with protein migration are excised. This process is followed by in-gel proteolysis in the presence of the AQUA peptides and LC-SRM analysis. (See Gerber et al. supra.) AQUA peptides are spiked in to the complex peptide mixture obtained by digestion of the whole cell lysate with a proteolytic enzyme and subjected to immunoaffinity purification as described above. The retention time and fragmentation pattern of the native peptide formed by digestion (e.g. trypsinization) is identical to that of the AQUA internal standard peptide determined previously; thus, LC-MS/MS analysis using an SRM experiment results in the highly specific and sensitive measurement of both internal standard and analyte directly from extremely complex peptide mixtures. Because an absolute amount of the AQUA peptide is added (e.g. 250 fmol), the ratio of the areas under the curve can be used to determine the precise expression levels of a protein or phosphorylated form of a protein in the original cell lysate. In addition, the internal standard is present during in-gel digestion as native peptides are formed, such that peptide extraction efficiency from gel pieces, absolute losses during sample handling (including vacuum centrifugation), and variability during introduction into the LC-MS system do not affect the determined ratio of native and AQUA peptide abundances.

An AQUA peptide standard is developed for a known phosphorylation site sequence previously identified by the IAP-LC-MS/MS method within in a target protein. One AQUA peptide incorporating the phosphorylated form of the particular residue within the site may be developed, and a second AQUA peptide incorporating the non-phosphorylated form of the residue developed. In this way, the two standards may be used to detect and quantify both the phosphorylated and non-phosphorylated forms of the site in a biological sample.

Peptide internal standards may also be generated by examining the primary amino acid sequence of a protein and determining the boundaries of peptides produced by protease cleavage. Alternatively, a protein may actually be digested with a protease and a particular peptide fragment produced can then sequenced. Suitable proteases include, but are not limited to, serine proteases (e.g. trypsin, hepsin), metallo proteases (e.g. PUMP1), chymotrypsin, cathepsin, pepsin, thermolysin, carboxypeptidases, etc.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Thus, a peptide is preferably at least about 6 amino acids. The size of the peptide is also optimized to maximize ionization frequency. Thus, peptides longer than about 20 amino acids are not preferred. The preferred ranged is about 7 to 15 amino acids. A peptide sequence is also selected that is not likely to be chemically reactive during mass spectrometry, thus sequences comprising cysteine, tryptophan, or methionine are avoided.

A peptide sequence that does not include a modified region of the target region may be selected so that the peptide internal standard can be used to determine the quantity of all forms of the protein. Alternatively, a peptide internal standard encompassing a modified amino acid may be desirable to detect and quantify only the modified form of the target protein. Peptide standards for both modified and unmodified regions can be used together, to determine the extent of a modification in a particular sample (i.e. to determine what fraction of the total amount of protein is represented by the modified form). For example, peptide standards for both the phosphorylated and unphosphorylated form of a protein known to be phosphorylated at a particular site can be used to quantify the amount of phosphorylated form in a sample.

The peptide is labeled using one or more labeled amino acids (i.e. the label is an actual part of the peptide) or less preferably, labels may be attached after synthesis according to standard methods. Preferably, the label is a mass-altering label selected based on the following considerations: The mass should be unique to shift fragments masses produced by MS analysis to regions of the spectrum with low background; the ion mass signature component is the portion of the labeling moiety that preferably exhibits a unique ion mass signature in MS analysis; the sum of the masses of the constituent atoms of the label is preferably uniquely different than the fragments of all the possible amino acids. As a result, the labeled amino acids and peptides are readily distinguished from unlabeled ones by the ion/mass pattern in the resulting mass spectrum. Preferably, the ion mass signature component imparts a mass to a protein fragment that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions, and the labeled tag preferably remains soluble in the MS buffer system of choice. The label preferably does not suppress the ionization efficiency of the protein and is not chemically reactive. The label may contain a mixture of two or more isotopically distinct species to generate a unique mass spectrometric pattern at each labeled fragment position. Stable isotopes, such as $^{2}H$, $^{13}C$, $^{15}N$, $^{17}O$, $^{18}O$, or $^{34}S$, are among preferred labels. Pairs of peptide internal standards that incorporate a different isotope label may also be prepared. Preferred amino acid residues into which a heavy isotope label may be incorporated include leucine, proline, valine, and phenylalanine.

Peptide internal standards are characterized according to their mass-to-charge (m/z) ratio, and preferably, also according to their retention time on a chromatographic column (e.g. an HPLC column). Internal standards that co-elute with unlabeled peptides of identical sequence are selected as optimal internal standards. The internal standard is then analyzed by fragmenting the peptide by any suitable means, for example by collision-induced dissociation (CID) using, e.g., argon or helium as a collision gas. The fragments are then analyzed, for example by multi-stage mass spectrometry ($MS^n$) to obtain a fragment ion spectrum, to obtain a peptide fragmentation signature. Preferably, peptide fragments have significant differences in m/z ratios to enable peaks corresponding to each fragment to be well separated, and a signature is that is unique for the target peptide is obtained. If a suitable fragment signature is not obtained at the first stage, additional stages of MS are performed until a unique signature is obtained.

Fragment ions in the MS/MS and $MS^3$ spectra are typically highly specific for the peptide of interest, and, in conjunction with LC methods, allow a highly selective means of detecting and quantifying a target peptide/protein in a complex protein mixture, such as a cell lysate, containing many thousands or tens of thousands of proteins. Any biological sample potentially containing a target protein/peptide of interest may be assayed. Crude or partially purified cell extracts are preferably employed. Generally, the sample has at least 0.01 mg of protein, typically a concentration of 0.1-10 mg/mL, and may be adjusted to a desired buffer concentration and pH.

A known amount of a labeled peptide internal standard, preferably about 10 femtomoles, corresponding to a target protein to be detected/quantified is then added to a biological sample, such as a cell lysate. The spiked sample is then digested with one or more protease(s) for a suitable time period to allow digestion. A separation is then performed (e.g. by HPLC, reverse-phase HPLC, capillary electrophoresis, ion exchange chromatography, etc.) to isolate the labeled internal standard and its corresponding target peptide from other peptides in the sample. Microcapillary LC is a preferred method.

Each isolated peptide is then examined by monitoring of a selected reaction in the MS. This involves using the prior knowledge gained by the characterization of the peptide internal standard and then requiring the MS to continuously monitor a specific ion in the MS/MS or $MS^n$ spectrum for both the peptide of interest and the internal standard. After elution, the area under the curve (AUC) for both peptide standard and target peptide peaks are calculated. The ratio of the two areas provides the absolute quantification that can be normalized for the number of cells used in the analysis and the protein's molecular weight, to provide the precise number of copies of the protein per cell. Further details of the AQUA methodology are described in Gygi et al., and Gerber et al. supra.

In accordance with the present invention, AQUA internal peptide standards (heavy-isotope labeled peptides) may now be produced, as described above, for any of the 95 novel T-cell receptor signaling protein phosphorylation sites disclosed herein (see Table 1/FIG. 2). Peptide standards for a given phosphorylation site (e.g. the tyrosine 123 site in Max—see Row 82 of Table 1) may be produced for both the phosphorylated and non-phosphorylated forms of the site (e.g. see Max site sequence in Column G, Row 82 of Table 1) and such standards employed in the AQUA methodology to detect and quantify both forms of such phosphorylation site in a biological sample.

The phosphorylation site peptide sequences disclosed herein (see Column G of Table 1/FIG. 2) are particularly well suited for development of corresponding AQUA peptides, since the IAP method by which they were identified (see Part A above and Example 1) inherently confirmed that such peptides are in fact produced by enzymatic digestion (trypsinization) and are in fact suitably fractionated/ionized in MS/MS. Thus, heavy-isotope labeled equivalents of these peptides (both in phosphorylated and unphosphorylated form) can be readily synthesized and their unique MS and LC-SRM signature determined, so that the peptides are validated as AQUA peptides and ready for use in quantification experiments.

Accordingly, the invention provides heavy-isotope labeled peptides (AQUA peptides) for the detection and/or quantification of any of the T-cell receptor signaling protein phosphorylation sites disclosed in Table 1/FIG. 2 (see Column G) and/or their corresponding parent proteins/polypeptides (see Column A). Each such phosphorylation sequence may be considered a preferred AQUA peptide of the invention. Optimally, an AQUA peptide of the invention consists of a phosphorylation site sequence enumerated in Table 1. For example, an AQUA peptide comprising the sequence GAD-SApYYQVGQTGK (SEQ ID NO: 52) (where pY may be either phosphotyrosine or tyrosine, and where V=labeled valine (e.g. $^{14}C$)) is provided for the quantification of phosphorylated (or non-phosphorylated) PIP5K (Tyr1772) in a biological sample (see Row 53 of Table 1, tyrosine 1772 being the phosphorylatable residue within the site). However, it will be appreciated that a larger AQUA peptide comprising the disclosed phosphorylation site sequence (and additional residues downstream or upstream of it) may also be constructed. Similarly, a smaller AQUA peptide comprising less than all of the residues of a disclosed phosphorylation site sequence (but still comprising the phosphorylatable residue enumerated in Column F of Table 1/FIG. 2) may alternatively be constructed. Such larger or shorter AQUA peptides are within the scope of the present invention, and the selection and production of preferred AQUA peptides may be carried out as described above (see Gygi et al., Gerber et al. supra.).

Certain particularly preferred subsets of AQUA peptides provided by the invention are described above (corresponding to particular protein types/groups in Table 1, for example, Adaptor/Scaffold proteins or RNA Binding Proteins). Example 4 is provided to further illustrate the construction and use, by standard methods described above, of exemplary AQUA peptides provided by the invention. For example, AQUA peptides corresponding to the both the phosphorylated and non-phosphorylated forms of the disclosed UBE1 tyrosine 55 phosphorylation site (NGSEADIDEGLpYSR (SEQ ID NO: 91)—see Row 92 of Table 1/FIG. 2) may be used to quantify the amount of phosphorylated UBE1 (Tyr55) in biological sample, e.g. a T-cell sample (or a sample before or after treatment with a test drug).

AQUA peptides of the invention may also be employed within a kit that comprises one or multiple AQUA peptide(s) provided herein (for the quantification of an T-cell receptor signal transduction protein disclosed in Table 1), and, optionally, a second detecting reagent conjugated to a detectable group. For example, a kit may include AQUA peptides for both the phosphorylation and non-phosphorylated form of a phosphorylation site disclosed herein. The reagents may also include ancillary agents such as buffering agents and protein stabilizing agents, e.g., polysaccharides and the like. The kit may further include, where necessary, other members of the signal-producing system of which system the detectable group is a member (e.g., enzyme substrates), agents for reducing background interference in a test, control reagents, apparatus for conducting a test, and the like. The test kit may be packaged in any suitable manner, typically with all elements in a single container along with a sheet of printed instructions for carrying out the test.

AQUA peptides provided by the invention will be highly useful in the further study of signal transduction anomalies underlying diseases, including lymphomas, involving altered T-cell receptor signaling, and in identifying diagnostic/biomarkers of these diseases, new potential drug targets, and/or in monitoring the effects of test compounds on T-cell receptor signal transduction proteins and pathways.

D. Immunoassay Formats

Antibodies provided by the invention may be advantageously employed in a variety of standard immunological assays (the use of AQUA peptides provided by the invention is described separately above). Assays may be homogeneous assays or heterogeneous assays. In a homogeneous assay the immunological reaction usually involves a phosphorylation-site specific antibody of the invention, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels that may be employed include free radicals, radioisotopes, fluorescent dyes, enzymes, bacteriophages, coenzymes, and so forth.

In a heterogeneous assay approach, the reagents are usually the specimen, a phosphorylation-site specific antibody of the invention, and suitable means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the specimen. Means for producing a detectable signal include the use of radioactive labels, fluorescent labels, enzyme labels, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Immunoassay formats and variations thereof that may be useful for carrying out the methods disclosed herein are well known in the art. See generally E. Maggio, Enzyme-Immunoassay, (1980) (CRC Press, Inc., Boca Raton, Fla.); see also, e.g., U.S. Pat. No. 4,727,022 (Skold et al., "Methods for Modulating Ligand-Receptor Interactions and their Application"); U.S. Pat. No. 4,659,678 (Forrest et al., "Immunoassay of Antigens"); U.S. Pat. No. 4,376,110 (David et al., "Immunometric Assays Using Monoclonal Antibodies"). Conditions suitable for the formation of reagent-antibody complexes are well described. See id. Monoclonal antibodies of the invention may be used in a "two-site" or "sandwich" assay, with a single cell line serving as a source for both the labeled monoclonal antibody and the bound monoclonal antibody. Such assays are described in U.S. Pat. No. 4,376,110. The concentration of detectable reagent should be sufficient such that the binding of a target T-cell receptor signal transduction protein is detectable compared to background.

Phosphorylation site-specific antibodies disclosed herein may be conjugated to a solid support suitable for a diagnostic assay (e.g., beads, plates, slides or wells formed from materials such as latex or polystyrene) in accordance with known techniques, such as precipitation. Antibodies, or other target protein or target site-binding reagents, may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

Antibodies of the invention may also be optimized for use in a flow cytometry assay to determine the activation/phosphorylation status of a target T-cell receptor signaling protein in patients before, during, and after treatment with a drug targeted at inhibiting phosphorylation at such a protein at the phosphorylation site disclosed herein. For example, bone marrow cells or peripheral blood cells from patients may be analyzed by flow cytometry for target T-cell receptor signaling protein phosphorylation, as well as for markers identifying various hematopoietic cell types. In this manner, activation status of the malignant cells may be specifically characterized. Flow cytometry may be carried out according to standard methods. See, e.g. Chow et al., *Cytometry (Communications in Clinical Cytometry)* 46: 72-78 (2001). Briefly and by way of example, the following protocol for cytometric analysis may be employed: fixation of the cells with 1% para-formaldehyde for 10 minutes at 37° C. followed by permeabilization in 90% methanol for 30 minutes on ice. Cells may then be stained with the primary antibody (a phospho-specific antibody of the invention), washed and labeled with a fluorescent-labeled secondary antibody. Alternatively, the cells may be stained with a fluorescent-labeled primary antibody. The cells would then be analyzed on a flow cytometer (e.g. a Beckman Coulter EPICS-XL) according to the specific protocols of the instrument used. Such an analysis would identify the presence of activated T-cell receptor signal transduction protein(s) in the diseased cells and reveal the drug response on the targeted protein.

Alternatively, antibodies of the invention may be employed in immunohistochemical (IHC) staining to detect differences in signal transduction or protein activity using normal and diseased tissues. IHC may be carried out according to well-known techniques. See, e.g., ANTIBODIES: A LABORATORY MANUAL, supra. Briefly, paraffin-embedded tissue (e.g. tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

Antibodies of the invention may be also be optimized for use in other clinically-suitable applications, for example bead-based multiplex-type assays, such as IGEN, Luminex™ and/or Bioplex™ assay formats, or otherwise optimized for antibody arrays formats, such as reversed-phase array applications (see, e.g. Paweletz et al., *Oncogene* 20(16): 1981-89 (2001)). Accordingly, in another embodiment, the invention provides a method for the multiplex detection of T-cell receptor signaling protein phosphorylation in a biological sample, the method comprising utilizing at two or more antibodies or AQUA peptides of the invention to detect the presence of two or more phosphorylated T-cell receptor signaling proteins enumerated in Column A of Table 1/FIG. 2. In one preferred embodiment, two to five antibodies or AQUA peptides of the invention are employed in the method. In another preferred embodiment, six to ten antibodies or AQUA peptides of the invention are employed, while in another preferred embodiment eleven to twenty such reagents are employed.

Antibodies and/or AQUA peptides of the invention may also be employed within a kit that comprises at least one phosphorylation site-specific antibody or AQUA peptide of the invention (which binds to or detects an T-cell receptor signaling protein/site disclosed in Table 1), and, optionally, a second antibody conjugated to a detectable group. In some embodies, the kit is suitable for multiplex assays and comprises two or more antibodies or AQUA peptides of the invention, and in some embodiments, comprises two to five, six to ten, or eleven to twenty reagents of the invention. The kit may also include ancillary agents such as buffering agents and protein stabilizing agents, e.g., polysaccharides and the like. The kit may further include, where necessary, other members of the signal-producing system of which system the detectable group is a member (e.g., enzyme substrates), agents for reducing background interference in a test, control reagents, apparatus for conducting a test, and the like. The test kit may be packaged in any suitable manner, typically with all elements in a single container along with a sheet of printed instructions for carrying out the test.

The following Examples are provided only to further illustrate the invention, and are not intended to limit its scope, except as provided in the claims appended hereto. The present invention encompasses modifications and variations of the methods taught herein which would be obvious to one of ordinary skill in the art.

EXAMPLE 1

Isolation of Phosphotyrosine-Containing Peptides from Extracts of Activated Jurkat Cells and Identification of Novel Phosphorylation Sites In order to discover previously unknown T-cell receptor signaling protein phosphorylation sites, IAP isolation techniques were employed to identify phosphotyrosine-containing peptides in cell extracts from Jurkat cells treated with pervanadate in order to stimulate tyrosine phosphorylation.

Tryptic phosphotyrosine peptides were purified and analyzed from extracts of the Jurkat cell line as follows. Cells were cultured in RPMI medium supplemented with 10% bovine serum and penicillin/streptomycin. Cells were cultured to a density of $1.2\times10^6$ cells/ml and were washed in PBS at room temperature, then resuspended in PBS at $7\times10^7$ cells/ml. After preincubation at 37° C. for 20 min, calyculin A and sodium pervanadate were added to final concentrations of 50 ng/ml and 1 mM, respectively, and cells were incubated for 20 min at 37° C. After centrifugation at room temperature, cells were resuspended at $1.25\times10^8$ cells/ml in lysis buffer (20 mM HEPES pH 8.0, 9 M urea, 1 mM sodium vanadate) and sonicated. Karpas 299 and SU-DHL-1 cells cultured to a density of $0.5$-$0.8\times10^6$ cells/ml were washed with PBS at 4° C., resuspended in lysis buffer as above and sonicated.

Sonicated cell lysates were cleared by centrifugation at $20{,}000\times g$, and proteins were reduced with DTT at a final concentration of 4.1 mM and alkylated with iodoacetamide at 8.3 mM. For digestion with trypsin, protein extracts were diluted in 20 mM HEPES pH 8.0 to a final concentration of 2 M urea and immobilized TLCK-trypsin (Pierce) was added at 1-2.5 ml beads (200 TAME units trypsin/ml) per $10^9$ cells. Digestion was performed for 1-2 days at room temperature.

Trifluoroacetic acid (TFA) was added to protein digests to a final concentration of 1%, precipitate was removed by centrifugation, and digests were loaded onto Sep-Pak $C_{18}$ columns (Waters) equilibrated with 0.1% TFA. A column volume of 0.7-1.0 ml was used per $2\times10^8$ cells. Columns were washed with 15 volumes of 0.1% TFA, followed by 4 volumes of 5% acetonitrile (MeCN) in 0.1% TFA. Peptide fraction I was obtained by eluting columns with 2 volumes each of 8, 12, and 15% MeCN in 0.1% TFA and combining the eluates. Fractions II and III were a combination of eluates after eluting columns with 18, 22, 25% MeCN in 0.1% TFA and with 30, 35, 40% MeCN in 0.1% TFA, respectively. All peptide fractions were lyophilized.

Peptides from each fraction corresponding to $2\times10^8$ cells were dissolved in 1 ml of IAP buffer (20 mM Tris/HCl or 50 mM MOPS pH 7.2, 10 mM sodium phosphate, 50 mM NaCl) and insoluble matter (mainly in peptide fractions III) was removed by centrifugation. IAP was performed on each peptide fraction separately. The phosphotyrosine monoclonal antibody P-Tyr-100 (Cell Signaling Technology, Inc., catalog number 9411) was coupled at 4 mg/ml beads to protein G agarose (Roche). Immobilized antibody (15 µl, 60 µg) was added as 1:1 slurry in IAP buffer to 1 ml of each peptide fraction, and the mixture was incubated overnight at 40° C. with gentle rotation. The immobilized antibody beads were washed three times with 1 ml IAP buffer and twice with 1 ml water, all at 4° C. Peptides were eluted from beads by incubation with 75 µl of 0.1% TFA at room temperature for 10 min.

Analysis by MALDI-TOF Mass Spectrometry.

A thin layer of α-cyano-4-hydroxy-cinnamic acid (ACHA) matrix was applied to a Bruker 384-spot MALDI target by spreading 5 µl of a saturated solution in MeCN/water (2/1, v/v) over an entire row of spots on the target; drying occurred in 2-5 sec. The IAP eluate (10 µl) was loaded onto an 0.2 µl C-18 ZipTip (Millipore), which then was washed with 5% formic acid. Peptide was eluted with 1 µl of 10 mg/ml ACHA in 60% methanol, 5% formic acid onto the MALDI target containing the thin layer of matrix. Samples were analyzed on a Bruker BiFlex III MALDI-TOF instrument in positive ion mode.

Analysis by LC-MS/MS Mass Spectrometry.

40 µl of IAP eluate were purified by 0.2 µl C-18 ZipTip (Millipore). Peptides were eluted from the microcolumns with 1 µl of 40% MeCN, 0.1% TFA (fractions I and II) or 1 µl of 60% MeCN, 0.1% TFA (fraction III) into 7.6 µl of 0.4% acetic acid/0.005% heptafluorobutyric acid. This sample was loaded onto a 10 cm×75 µm PicoFrit capillary column (New Objective) packed with Magic C18 AQ reversed-phase resin (Michrom Bioresources) using a Famos autosampler with an inert sample injection valve (Dionex). The column was then developed with a 45-min linear gradient of acetonitrile delivered at 200 nl/min (Ultimate, Dionex), and tandem mass spectra were collected in a data-dependent manner with an LCQ Deca XP Plus ion trap mass spectrometer essentially as described by Gygi et al., supra.

Database Analysis & Assignments.

MS/MS spectra were evaluated using TurboSequest in the Sequest Browser package (v. 27, rev. 12) supplied as part of BioWorks 3.0 (ThermoFinnigan). Individual MS/MS spectra were extracted from the raw data file using the Sequest Browser program CreateDta, with the following settings: bottom MW, 700; top MW, 4,500; minimum number of ions, 20; minimum TIC, $4\times10^5$; and precursor charge state, unspecified. Spectra were extracted from the beginning of the raw data file before sample injection to the end of the eluting gradient. The IonQuest and VuDta programs were not used to further select MS/MS spectra for Sequest analysis. MS/MS spectra were evaluated with the following TurboSequest parameters: peptide mass tolerance, 2.5; fragment ion tolerance, 0.0; maximum number of differential amino acids per modification, 4; mass type parent, average; mass type fragment, average; maximum number of internal cleavage sites, 10; neutral losses of water and ammonia from b and y ions were considered in the correlation analysis. Proteolytic enzyme was specified except for spectra collected from elastase digests.

Searches were performed against the NCBI human protein database (released on Apr. 29, 2003 and containing 37,490 protein sequences). Cysteine carboxamidomethylation was specified as a static modification, and phosphorylation was allowed as a variable modification on serine, threonine, and tyrosine residues or on tyrosine residues alone. It was determined that restricting phosphorylation to tyrosine residues had little effect on the number of phosphorylation sites assigned.

In proteomics, it is desirable to validate protein identifications based solely on the observation of a single peptide in one experimental result, in order to indicate that the protein is, in fact, present in a sample. This has led to the development of statistical methods for validating peptide assignments, which are not yet universally accepted, and guidelines for the publication of protein and peptide identification results (see Carr et al. Mol Cell Proteomics 3: 531-533 (2004), which were followed in this Example. However, because the immunoaffinity strategy separates phosphorylated peptides from unphosphorylated peptides, observing just one phosphopeptide from a protein is a common result, since many phosphorylated proteins have only one tyrosine-phosphorylated site. For this reason, it is appropriate to use additional criteria to validate phosphopeptide assignments. Assignments are likely to be correct if any of these additional criteria are met: (i) the same sequence is assigned to co-eluting ions with different charge states, since the MS/MS spectrum changes markedly with charge state; (ii) the site is found in more than one peptide sequence context due to sequence overlaps from incomplete proteolysis or use of proteases other than trypsin; (iii) the site is found in more than one peptide sequence context due to homologous but not identical protein isoforms; (iv) the site is found in more than one peptide sequence context due to homologous but not identical proteins among species; and (v) sites validated by MS/MS analysis of synthetic phosphopeptides corresponding to assigned sequences, since the ion trap mass spectrometer produces highly reproducible MS/MS spectra. The last criterion is routinely employed to confirm novel site assignments of particular interest.

All spectra and all sequence assignments made by Sequest were imported into a relational database. Assigned sequences were accepted or rejected following a conservative, two-step process. In the first step, a subset of high-scoring sequence assignments was selected by filtering for XCorr values of at least 1.5 for a charge state of +1, 2.2 for +2, and 3.3 for +3, allowing a maximum RSp value of 10. Assignments in this subset were rejected if any of the following criteria were satisfied: (i) the spectrum contained at least one major peak (at least 10% as intense as the most intense ion in the spectrum) that could not be mapped to the assigned sequence as an a, b, or y ion, as an ion arising from neutral-loss of water or ammonia from a b or y ion, or as a multiply protonated ion; (ii) the spectrum did not contain an series of b or y ions equivalent to at least six uninterrupted residues; or (iii) the sequence was not observed at least five times in all the studies we have conducted (except for overlapping sequences due to incomplete proteolysis or use of proteases other than trypsin). In the second step, assignments with below-threshold scores were accepted if the low-scoring spectrum showed a high degree of similarity to a high-scoring spectrum collected in another study, which simulates a true reference library-searching strategy. All spectra supporting the final list of 95 assigned sequences enumerated in Table 1/FIG. 2 herein were reviewed by at least three people to establish their credibility.

EXAMPLE 2

Production of Phospho-specific Polyclonal Antibodies for the Detection of T-cell Receptor Signaling Protein Phosphorylation Polyclonal antibodies that specifically bind a T-cell receptor signal transduction protein only when phosphorylated at the respective phosphorylation site disclosed herein (see Table 1) are produced according to standard methods by first constructing a synthetic peptide antigen comprising the phosphorylation site sequence and then immunizing an animal to raise antibodies against the antigen, as further described below. Production of exemplary polyclonal antibodies is provided below.

A. Cdk6 (Tyrosine 24).

A 15 amino acid phospho-peptide antigen, AEIGEGAy*GKVFKAR (SEQ ID NO: 61) (where y*=phosphotyrosine), that corresponds to the tyrosine 24 phosphorylation site in human Cdk6 kinase (see Row 62 of Table 1), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phospho-specific Cdk6 (Tyr24) polyclonal antibodies as described in Immunization/Screening below.

B. ZAP70 (Tyrosine 248).

A 15 amino acid phospho-peptide antigen, LKADGLly*CLKEACP (SEQ ID NO: 63) (where y*=phosphotyrosine), that corresponds to the tyrosine 248 phosphorylation site in human ZAP70 kinase (see Row 64 of Table 1), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phospho-specific ZAP70 (Tyr248) polyclonal antibodies as described in Immunization/Screening below.

C. SIT (Tyrosine 95).

A 15 amino acid phospho-peptide antigen, PLYGNLHy*LQTGRLS (SEQ ID NO: 12) (where y*=phosphotyrosine) that corresponds to the tyrosine 95 phosphorylation site in human SIT protein (see Row 13 of Table 1), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phospho-specific SIT (Tyr95) antibodies as described in Immunization/Screening below.

Immunization/Screening.

A synthetic phospho-peptide antigen as described in A-C above is coupled to KLH, and rabbits are injected intradermally (ID) on the back with antigen in complete Freunds adjuvant (500 µg antigen per rabbit). The rabbits are boosted with same antigen in incomplete Freund adjuvant (250 µg antigen per rabbit) every three weeks. After the fifth boost, bleeds are collected. The sera are purified by Protein A-affinity chromatography by standard methods (see ANTIBODIES: A LABORATORY MANUAL, Cold Spring Harbor, supra.). The eluted immunoglobulins are further loaded onto a non-phosphorylated synthetic peptide antigen-resin Knotes column to pull out antibodies that bind the non-phosphorylated form of the phosphorylation site. The flow through fraction is collected and applied onto a phospho-synthetic peptide antigen-resin column to isolate antibodies that bind the phosphorylated form of the site. After washing the column extensively, the bound antibodies (i.e. antibodies that bind a phosphorylated peptide described in A-C above, but do not bind the non-phosphorylated form of the peptide, are eluted and kept in antibody storage buffer.

The isolated antibody is then tested for phospho-specificity using Western blot assay using an appropriate cell line that expresses (or overexpresses) target phospho-protein (i.e. phosphorylated Cdk6, ZAP70, or SIT), for example, Jurkat cells. Cells are cultured in RPMI medium supplemented with 10% FCS and penicillin/streptomycin. Before stimulation, the cells are starved in serum-free RPMI medium for 4 hours. The cells are then stimulated with ligand (e.g. 50 ng/ml) for 5 minutes. Cell are collected, washed with PBS and directly lysed in cell lysis buffer. The protein concentration of cell lysates are then measured. The loading buffer is added into cell lysate and the mixture is boiled at 100° C. for 5 minutes. 20 µl (10 µg protein) of sample is then added onto 7.5% SDS-PAGE gel.

A standard Western blot may be performed according to the Immunoblotting Protocol set out in the CELL SIGNALING TECHNOLOGY, INC. 2003-04 Catalogue, p. 390. The isolated phospho-specific antibody is used at dilution 1:1000. Phosphorylation-site specificity of the antibody will be shown by binding of only the phosphorylated form of the target protein. Isolated phospho-specific polyclonal antibody does not recognize the target protein when not phosphorylated at the appropriate phosphorylation site in the non-stimulated cells (e.g. ZAP70 is not bound when not phosphorylated at tyrosine 248).

In order to confirm the specificity of the isolated antibody, different cell lysates containing various phosphorylated signal transduction proteins other than the target protein are prepared. The Western blot assay is preformed again using these cell lysates. The phospho-specific polyclonal antibody isolated as described above is used (1:1000 dilution) to test reactivity with the different phosphorylated non-target proteins on Western blot membrane. The phospho-specific antibody does not significantly cross-react with other phosphorylated signal transduction proteins, although occasionally slight binding with a highly-homologous phosphorylation-site on another protein may be observed. In such case the antibody may be further purified using affinity chromatography, or the specific immunoreactivity cloned by rabbit hybridoma technology.

EXAMPLE 3

Production of Phospho-Specific Monoclonal Antibodies for the Detection of T-Cell Receptor Signaling Protein Phosphorylation Monoclonal antibodies that specifically bind a T-cell receptor signal transduction protein only when phosphorylated at the respective phosphorylation site disclosed herein (see Table 1) are produced according to standard methods by first constructing a synthetic peptide antigen comprising the phosphorylation site sequence and then immunizing an animal to raise antibodies against the antigen, and harvesting spleen cells from such animals to produce fusion hybridomas, as further described below. Production of exemplary monoclonal antibodies is provided below.

A. Cdk6 (Tyrosine 13).

A 15 amino acid phospho-peptide antigen, LCRADQQY*ECVAEIG (SEQ ID NO: 60) (where y*=phosphotyrosine) that corresponds to the tyrosine 13 phosphorylation site in human Cdk6 kinase (see Row 61 of Table 1), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phospho-specific monoclonal Cdk6 (Tyr13) antibodies as described in Immunization/Fusion/Screening below.

B. FAF-X (Tyrosine 2533).

A 15 amino acid phospho-peptide antigen, GQRAQENY*EGSEEVS (SEQ ID NO: 59) (where y*=phosphotyrosine) that corresponds to the tyrosine 2533 phosphorylation site in human FAF-X protease (see Row 60 of Table 1), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phospho-specific monoclonal FAF-X (Tyr2533) antibodies as described in Immunization/Fusion/Screening below.

C. Cortactin-a (Tyrosine 453).

A 15 amino acid phospho-peptide antigen, YSMEAAMDy*REASSQQ (SEQ ID NO: 43) (where y*=phosphotyrosine) that corresponds to the tyrosine 453 phosphorylation site in human Cortacin (isoform a) protein (see Row 44 of Table 1), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phospho-specific monoclonal Cortactin-a (Tyr453) antibodies as described in Immunization/Fusion/Screening below.

Immunization/Fusion/Screening.

A synthetic phospho-peptide antigen as described in A-C above is coupled to KLH, and BALB/C mice are injected intradermally (ID) on the back with antigen in complete Freunds adjuvant (e.g. 50 µg antigen per mouse). The mice are boosted with same antigen in incomplete Freund adjuvant (e.g. 25 µg antigen per mouse) every three weeks. After the fifth boost, the animals are sacrificed and spleens are harvested.

Harvested spleen cells are fused to SP2/0 mouse myeloma fusion partner cells according to the standard protocol of Kohler and Milstein (1975). Colonies originating from the fusion are screened by ELISA for reactivity to the phospho-peptide and non-phospho-peptide forms of the antigen and by Western blot analysis (as described in Example 1 above). Colonies found to be positive by ELISA to the phosphopeptide while negative to the non-phospho-peptide are further characterized by Western blot analysis. Colonies found to be positive by Western blot analysis are subcloned by limited dilution. Mouse ascites are produced from a single clone obtained from subcloning, and tested for phospho-specificity (against the Cdk6, FAF-X, or Cortactin-a phospho-peptide antigen, as the case may be) on ELISA. Clones identified as positive on Western blot analysis using cell culture supernatant as having phospho-specificity, as indicated by a strong band in the induced lane and a weak band in the uninduced lane of the blot, are isolated and subcloned as clones producing monoclonal antibodies with the desired specificity.

Ascites fluid from isolated clones may be further tested by Western blot analysis. The ascites fluid should produce similar results on Western blot analysis as observed previously with the cell culture supernatant, indicating phospho-specificity against the phosphorylated target (e.g. FAF-X phosphorylated at tyrosine 2533).

EXAMPLE 4

Production and Use of AQUA Peptides for the Quantification of T-cell Receptor Signaling Protein Phosphorylation Heavy-isotope labeled peptides (AQUA peptides (internal standards)) for the detection and quantification of an T-cell receptor signal transduction protein only when phosphorylated at the respective phosphorylation site disclosed herein (see Table 1) are produced according to the standard AQUA methodology (see Gygi et al., Gerber et al., supra.) methods by first constructing a synthetic peptide standard corresponding to the phosphorylation site sequence and incorporating a heavy-isotope label. Subsequently, the $MS^n$ and LC-SRM signature of the peptide standard is validated, and the AQUA peptide is used to quantify native peptide in a biological sample, such as a digested cell extract. Production and use of exemplary AQUA peptides is provided below.

A. LPP (Tyrosine 317).

An AQUA peptide having a sequence corresponding to the tyrosine 317 phosphorylation site in human Lipoma-preferred-partner (LPP) protein, RNDSDPTy*GQQGHPN (y*=phosphotyrosine) (see Row 14 in Table 1 (SEQ ID NO: 13)) but incorporating $^{14}C/^{15}N$-labeled proline (indicated by bold P) is constructed according to standard synthesis techniques using, e.g., a Rainin/Protein Technologies, Inc., Symphony peptide synthesizer (see Merrifield, supra.) as further described below in Synthesis & MS/MS Signature. The LPP (Tyr317) AQUA peptide is then spiked into a biological sample to quantify the amount of phosphorylated LPP (Tyr317) in the sample, as further described below in Analysis & Quantification.

B. Ets-1 (Tyrosine 205).

An AQUA peptide having a sequence corresponding to the tyrosine 205 phosphorylation site in human Ets-1 transcription factor protein, SLKYENDy*PSVILRD (y*=phosphotyrosine) (see Row 78 in Table 1 (SEQ ID NO: 77)) but incorporating $^{14}C/^{15}N$-labeled leucine (indicated by bold L) is constructed according to standard synthesis techniques using, e.g., a Rainin/Protein Technologies, Inc., Symphony peptide synthesizer (see Merrifield, supra.) as further described below in Synthesis & MS/MS Signature. The Ets-1 (Tyr205) AQUA peptide is then spiked into a biological sample to quantify the amount of phosphorylated Ets-1 (Tyr205) in the sample, as further described below in Analysis & Quantification.

C. Bid (Tyrosine 54).

An AQUA peptide having a sequence corresponding to the tyrosine 54 phosphorylation site in human Bid protein, LAPQWEGy*DELQTDG (y*=phosphotyrosine) (see Row 18 in Table 1 (SEQ ID NO: 17)) but incorporating $^{14}C/^{15}N$-labeled leucine (indicated by bold L) is constructed according to standard synthesis techniques using, e.g., a Rainin/Protein Technologies, Inc., Symphony peptide synthesizer (see Merrifield, supra.) as further described below in Synthesis & MS/MS Signature. The Bid (Tyr54) AQUA peptide is then spiked into a biological sample to quantify the amount of phosphorylated Bid (Tyr54) in the sample, as further described below in Analysis & Quantification.

D. GIT2 (Tyrosine 492).

An AQUA peptide having a sequence corresponding to the tyrosine 492 phosphorylation site in human GIT2 protein, QVQTGSEy*TDTSNHS (y*=phosphotyrosine) (see Row 51 in Table 1 (SEQ ID NO: 50)) but incorporating $^{14}C/^{15}N$-labeled valine (indicated by bold V) is constructed according to standard synthesis techniques using, e.g., a Rainin/Protein Technologies, Inc., Symphony peptide synthesizer (see Merrifield, supra.) as further described below in Synthesis & MS/MS Signature. The GIT2 (Tyr492) AQUA peptide is then spiked into a biological sample to quantify the amount of phosphorylated GIT2 (Tyr492) in the sample, as further described below in Analysis & Quantification.

Synthesis & MS/MS Spectra.

Fluorenylmethoxycarbonyl (Fmoc)-derivatized amino acid monomers may be obtained from AnaSpec (San Jose, Calif.). Fmoc-derivatized stable-isotope monomers containing one $^{15}N$ and five to nine $^{13}C$ atoms may be obtained from Cambridge Isotope Laboratories (Andover, Mass.). Preloaded Wang resins may be obtained from Applied Biosystems. Synthesis scales may vary from 5 to 25 pmol. Amino acids are activated in situ with 1-H-benzotriazolium, 1-bis (dimethylamino) methylene]-hexafluorophosphate(1-),3-oxide:1-hydroxybenzotriazole hydrate and coupled at a 5-fold molar excess over peptide. Each coupling cycle is followed by capping with acetic anhydride to avoid accumulation of one-residue deletion peptide byproducts. After synthesis peptide-resins are treated with a standard scavenger-containing trifluoroacetic acid (TFA)-water cleavage solution, and the peptides are precipitated by addition to cold ether. Peptides (i.e. a desired AQUA peptide described in A-D above) are purified by reversed-phase C18 HPLC using standard TFA/acetonitrile gradients and characterized by matrix-assisted laser desorption ionization-time of flight (Biflex III, Bruker Daltonics, Billerica, Mass.) and ion-trap (ThermoFinnigan, LCQ DecaXP) MS.

MS/MS spectra for each AQUA peptide should exhibit a strong y-type ion peak as the most intense fragment ion that is suitable for use in an SRM monitoring/analysis. Reverse-phase microcapillary columns (0.1 Å~150-220 mm) are prepared according to standard methods. An Agilent 1100 liquid chromatograph may be used to develop and deliver a solvent gradient [0.4% acetic acid/0.005% heptafluorobutyric acid (HFBA)/7% methanol and 0.4% acetic acid/0.005% HFBA/65% methanol/35% acetonitrile] to the microcapillary column by means of a flow splitter. Samples are then directly loaded onto the microcapillary column by using a FAMOS inert capillary autosampler (LC Packings, San Francisco) after the flow split. Peptides are reconstituted in 6% acetic acid/0.01% TFA before injection.

Analysis & Quantification.

Target protein (e.g. a phosphorylated protein of A-D above) in a biological sample is quantified using a validated AQUA peptide (as described above). The IAP method is then applied to the complex mixture of peptides derived from proteolytic cleavage of crude cell extracts to which the AQUA peptides have been spiked in.

LC-SRM of the entire sample is then carried out. MS/MS may be performed by using a ThermoFinnigan (San Jose, Calif.) mass spectrometer (LCQ DecaXP ion trap or TSQ Quantum triple quadrupole). On the DecaXP, parent ions are isolated at 1.6 m/z width, the ion injection time being limited to 150 ms per microscan, with two microscans per peptide averaged, and with an AGC setting of $1\times10^8$; on the Quantum, Q1 is kept at 0.4 and Q3 at 0.8 m/z with a scan time of 200 ms per peptide. On both instruments, analyte and internal standard are analyzed in alternation within a previously known reverse-phase retention window; well-resolved pairs of internal standard and analyte are analyzed in separate retention segments to improve duty cycle. Data are processed by integrating the appropriate peaks in an extracted ion chromatogram (60.15 m/z from the fragment monitored) for the native and internal standard, followed by calculation of the ratio of peak areas multiplied by the absolute amount of internal standard (e.g., 500 fmol).

What is claimed is:

1. An isolated phosphorylation site-specific antibody that specifically binds a human T-cell receptor signaling protein, wherein said signaling protein is cdk6, only when said signaling protein is phosphorylated at the tyrosine at position 13, comprised within the phosphorylatable peptide sequence listed in SEQ ID NO: 60, wherein said antibody does not bind said signaling protein when not phosphorylated at said tyrosine.

2. An isolated phosphorylation site-specific antibody that specifically binds a human T-cell receptor signaling protein, wherein said signaling protein is cdk6, only when said signaling protein is phosphorylated at the tyrosine at position 24, comprised within the phosphorylatable peptide sequence listed in SEQ ID NO: 61, wherein said antibody does not bind said signaling protein when not phosphorylated at said tyrosine.

3. An isolated phosphorylation site-specific antibody that specifically binds a human T-cell receptor signaling protein, wherein said signaling protein is SR-protein-specific kinase, only when said signaling protein is phosphorylated at the tyrosine at position 318, comprised within the phosphorylatable peptide sequence listed in SEQ ID NO: 62, wherein said antibody does not bind said signaling protein when not phosphorylated at said tyrosine.

4. An isolated phosphorylation site-specific antibody that specifically binds a human T-cell receptor signaling protein, wherein said signaling protein is ZAP70, only when said signaling protein is phosphorylated at the tyrosine at position 248, comprised within the phosphorylatable peptide sequence listed in SEQ ID NO: 63, wherein said antibody does not bind said signaling protein when not phosphorylated at said tyrosine.

5. An immortalized cell line producing the antibody of any one of claims 1, 2, 3, or 4.

6. The cell line of claim 5, wherein said immortalized cell line is a rabbit hybridoma or a mouse hybridoma.

* * * * *